US010413226B2

(12) United States Patent
Tao et al.

(10) Patent No.: US 10,413,226 B2
(45) Date of Patent: Sep. 17, 2019

(54) NONCONTACT MONITORING OF BLOOD OXYGEN SATURATION USING CAMERA

(71) Applicants: Nongjian Tao, Fountain Hills, AZ (US); Dangdang Shao, Tempe, AZ (US)

(72) Inventors: Nongjian Tao, Fountain Hills, AZ (US); Dangdang Shao, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 379 days.

(21) Appl. No.: 15/337,947

(22) Filed: Oct. 28, 2016

(65) Prior Publication Data

US 2017/0127988 A1    May 11, 2017

Related U.S. Application Data

(60) Provisional application No. 62/252,949, filed on Nov. 9, 2015.

(51) Int. Cl.
*A61B 5/1455* (2006.01)
*A61B 5/0205* (2006.01)
(Continued)

(52) U.S. Cl.
CPC ........ *A61B 5/14552* (2013.01); *A61B 5/0205* (2013.01); *A61B 5/7257* (2013.01); *A61B 5/02416* (2013.01)

(58) Field of Classification Search
CPC . A61B 5/14552; A61B 5/7257; A61B 5/0205; A61B 5/02416
See application file for complete search history.

(56) References Cited

U.S. PATENT DOCUMENTS 5,462,439 A    10/1995 Keith
5,498,948 A    3/1996 Bruni et al.
(Continued)

FOREIGN PATENT DOCUMENTS

EP    2960862 A1    12/2015
WO    2016077690 A1    5/2016
(Continued)

OTHER PUBLICATIONS

Lempe, G. et al., "ROI selection for remote photoplethysmography", Proceedings Workshop Bildverarbeitung für die Medizin, Mar. 2013, pp. 99-103 <DOI:10.1007/978-3-642-36480-8_19>.
(Continued)

*Primary Examiner* — Eric F Winakur
*Assistant Examiner* — Abid A Mustansir
(74) *Attorney, Agent, or Firm* — George A. Leone; Citadel Patent Law

(57) ABSTRACT

A device for non-contact measurement of blood oxygen saturation ($SpO_2$) in a mammalian subject including a camera and one or more arrays of LEDs each having a first set of LEDs emitting near infrared (NIR), and the second set of LEDs emitting orange light located in an optical path adapted to transmit reflected light from a subject to the camera. A controller transmits a camera trigger to the camera, and is further coupled to transmit control signals to the one or more arrays of LEDs. A processor receives photoplethysmography (PPG) data signal values from the camera. The PPG data signal values are present in the reflected light and include pulsatile and non-pulsatile components. The processor determines $SpO_2$ values from the PPG data signal values from the measured ratios of pulsatile to non-pulsatile components of the PPG signals.

12 Claims, 13 Drawing Sheets

(51) Int. Cl.
*A61B 5/00* (2006.01)
*A61B 5/024* (2006.01)

(56) References Cited

U.S. PATENT DOCUMENTS

| | | | |
|---|---|---|---|
| 7,400,918 B2 | 7/2008 | Parker et al. | |
| 2007/0160286 A1 | 7/2007 | Haque | |
| 2009/0007412 A1 | 1/2009 | Wang et al. | |
| 2009/0147991 A1 | 6/2009 | Chau | |
| 2010/0111386 A1 | 5/2010 | El-Baz | |
| 2010/0292548 A1* | 11/2010 | Baker, Jr. | A61B 5/14551 600/324 |
| 2012/0046568 A1 | 2/2012 | Soatto et al. | |
| 2013/0271591 A1 | 10/2013 | Van Leest et al. | |
| 2013/0310700 A1 | 11/2013 | Wiard et al. | |
| 2013/0324830 A1 | 12/2013 | Bernal et al. | |
| 2014/0043457 A1 | 2/2014 | Stergiou | |
| 2014/0275832 A1 | 9/2014 | Muehlsteff et al. | |
| 2014/0275833 A1 | 9/2014 | Vanderpohl | |
| 2014/0276104 A1* | 9/2014 | Tao | A61B 5/7239 600/476 |
| 2015/0005646 A1 | 1/2015 | Balakrishnan et al. | |
| 2015/0018637 A1 | 1/2015 | Chen et al. | |
| 2015/0265187 A1 | 9/2015 | Bernal et al. | |
| 2016/0331991 A1* | 11/2016 | Kirenko | A61N 5/06 |
| 2017/0319114 A1* | 11/2017 | Kaestle | A61B 5/0077 |

FOREIGN PATENT DOCUMENTS

| | | |
|---|---|---|
| WO | 2017156084 A2 | 9/2017 |
| WO | 2018057753 A1 | 3/2018 |
| WO | 2018170009 A1 | 9/2018 |

OTHER PUBLICATIONS

Lucas, B. et al., "An Iterative Image Registration Technique with an Application to Stereo Vision", Proceedings of the 7th International Joint Conference on Artificial Intelligence (Vancouver, Canada, Aug. 24-28, 1981), 1981, pp. 674-679.

Maria, C. et al., "Feasibility of monitoring vascular ageing by multi-site photoplethysmography", Proceedings of Computing in Cardiology (Krakow, Poland, Sep. 9-12, 2012), 2012, pp. 817-820.

McDuff, D. et al., "Remote measurement of cognitive stress via heart rate variability", Proceedings of the 2014 IEEE Engineering in Medicine and Biology Society (Chicago, IL, Aug. 26-30, 2014), 2014 (Date Added to IEEE Xplore: (Nov. 2014), pp. 2957-2960 <DOI:10.1109/EMBC.2014.6944243>.

Migeotte, P-F. et al., "Three dimensional ballistocardiogrpahy: methodology and results from microgravity and dry immersion", 33rd Annual International Conference of the IEEE EMBS (Boston, MA, Aug. 30-Sep. 3, 2011), 2011 (Date Added to IEEE Xplore: Dec. 2011), pp. 4271-4274 <DOI:10.1109/IEMBS.2011.6091060>.

Mishra, S. et al., "Heart Rate Measurement Using Video in Different User States for Online HCI Applications", Procedia Computer Science, 2014, vol. 39, pp. 20-27 <DOI:10.1016/j.procs.2014.11.005>.

Moco, A. et al., "Ballistocardiographic Artifacts in PPG Imaging", IEEE Transactions on Biomedical Engineering, Sep. 2016 (IEEE published: Nov. 2015), vol. 63, No. 9, pp. 1804-1811 <DOI:10.1109/TBME.2015.2502398>.

Mukkamala, R. et al., "Towards ubiquitous blood pressure monitoring via pulse transit time: theory and practice", IEEE Transactions on Biomedical Engineering, Aug. 2015 (Date of Publication: Jun. 2015), vol. 62, No. 8, pp. 1879-1901 <DOI:10.1109/TBME.2015.2441951>.

Ngai, B. et al., "Comparative analysis of seismocardiogram waves with the ultra-low frequency ballistocardiogram", 31st Annual International Conference of the IEEE EMBS (Minneapolis, MN, Sep. 2-6, 2009), 2009 (Date Added to IEEE Xplore: Nov. 2009), pp. 2851-2854 <DOI:10.1109/IEMBS.2009.5333649>.

Nihon Kohden Corporation, "Company Profile: History 1950s" [online], Nihon Kohden Corporation, Jan. 2015 [retrieved Mar. 11, 2019 from archive.org, as it appeared on Jan. 8, 2015], retrieved from the internet: <URL:https://web.archive.org/web/20150108160752/https://www.nihonkohden.com/company/history/1950s.html>.

Nitzan, M. et al., "The difference in pulse transit time to the toe and finger measured by photoplethysmography", Physiological Measurement, Feb. 2002, vol. 23, No. 1, pp. 85-93 <DOI:10.1088/0967-3334/23/1/308>.

Paradiso, R., "Wearable health care system for vital signs monitoring", Proceedings of the 4th Annual IEEE Conference on Information Technology Applications in Biomedicine (Birmingham, UK, Apr. 24-26, 2003), Aug. 2003 (Date Added to IEEE Xplore: Aug. 2003), pp. 283-286 <DOI:10.1109/ITAB.2003.1222533>.

Patent Cooperation Treaty, International Searching Authority, International Search Report for PCT/US2015/060570, 2 pages, dated Feb. 1, 2016.

Patent Cooperation Treaty, International Searching Authority, Written Opinion for PCT/US2015/060570, 8 pages, dated Feb. 1, 2016.

Patent Cooperation Treaty, International Searching Authority, International Search Report for PCT/US2017/052744, 2 pages, dated Nov. 16, 2017.

Patent Cooperation Treaty, International Searching Authority, International Search Report for PCT/US2017/21302, 4 pages, dated Jul. 25, 2017.

Patent Cooperation Treaty, International Searching Authority, International Search Report for PCT/US2018/022252, dated Jun. 21, 2018.

Patent Cooperation Treaty, International Searching Authority, Written Opinion for PCT/US2017/021302, 5 pages, dated Jul. 25, 2017.

Patent Cooperation Treaty, International Searching Authority, Written Opinion for PCT/US2017/052744, 7 pages, dated Nov. 16, 2017.

Patent Cooperation Treaty, International Searching Authority, Written Opinion for PCT/US2018/022252, 5 pages, dated Jun. 21, 2018.

Patzak, A. et al., "Continuous blood pressure measurement using the pulse transit time: comparison to intra-arterial measurement", Blood Press, Apr. 2015, vol. 24, No. 4, pp. 217-221 <DOI:10.3109/08037051.2015.1030901>.

Pickett, J. et al., "Pulse oximetry and PPG measurements in plastic surgery", Proceedings of the 1997 IEEE Engineering in Medicine and Biology (Chicago, IL, Oct. 30-Nov. 2, 1997), 1997 (Date Added to IEEE Xplore: Aug. 2002), pp. 2330-2332 <DOI:10.1109/IEMBS.1997.758831>.

Pinheiro, E. et al., "Theory and developments in an unobtrusive cardiovascular system representataion: ballistocardiography", Open Biomedical Engineering Journal, Oct. 2010, vol. 4, pp. 201-216 <DOI:10.2174/1874120701004010201>.

Pinheiro, O. et al., "Blood pressure and heart rate variabilities estimation using Ballistocardiography", Proceedings of the 7th Conference on Telecommunications (Santa Maria da Feira, Portugal, May 2009), 2019, pp. 125-128.

Poh, M. et al., "Advancements in noncontact, multiparameter physiological measurements using a webcam", IEEE Transactions of Biomedical Engineering, Jan. 2011 (Date of Publication: Oct. 2010), vol. 58, No. 1, pp. 7-306 <DOI:10.1109/TBME.2010.2086456>.

Poh, M. et al., "Non-contact, automated cardiac pulse measurements using video imaging and blind source separation", Optics Express, May 2010, vol. 18, No. 10, pp. 10762-10774 <DOI:10.1364/OE.18.010762>.

Poon, C. et al., "Wearable Intelligent Systems for E-Health", Journal of Computing Science and Engineering, Sep. 2011, vol. 5, No. 3, pp. 246-256 <DOI:10.5626/JCSE.2011.5.3.246>.

Prahl, S., "Optical Absorption of Hemoglobin" [online], Oregon Medical Laser Center, Dec. 1999 [retrieved Mar. 11, 2019 from archive.org, as it appeared on Oct. 9, 2015], retrieved from the internet: <URL:https://web.archive.org/web/20151009033501/https://omlc.org/spectra/hemoglobin/>.

Prahl, S., "Tabulated Molar Extinction Coefficient for Hemoglobin in Water" [online], Oregon Medical Laser Center, Mar. 1998 [retrieved Mar. 11, 2019 from archive.org, as it appeared on Oct. 9,

(56) References Cited

OTHER PUBLICATIONS

2015], retrieved from the internet: <URL: https://web.archive.org/web/20151009033612/https://omlc.org/spectra/hemoglobin/summary.html>.
Rabben, S. et al., "An ultrasound-based method for determining pulse wave velocity in superficial arteries", Journal of Biomechanics, Oct. 2004, vol. 37, No. 10, pp. 1615-1622 <DOI:10.1016/j.jbiomech.2003.12.031>.
Reisner, A. et al., "Utility of the photoplethysmogram in circulatory monitoring", Anesthesiology, May 2008, vol. 108, No. 5, pp. 950-958 <DOI:10.1097/ALN.0b013e31816c89e1>.
Rusch, T. et al., "Alternate pulse oximetry algorithms for SpO/sub 2/ computation", Proceedings of the 16th Annual Conference of the IEEE Engineering in Medicine and Biology Society (Baltimore, MD, Nov. 3-6, 1994), 1994 (Date Added to IEEE Xplore: Aug. 2002), vol. 2, pp. 848-849 <DOI:10.1109/IEMBS.1994.415177>.
Rusch, T. et al., "Signal processing methods for pulse oximetry", Computers in Biology and Medicine, Mar. 1996, vol. 26, No. 2, pp. 143-159 <DOI:10.1016/0010-4825(95)00049-6>.
Sachdeva, S. et al., "Fitzpatrick skin typing: applications in dermatology", Indian Journal of Dermatology, Venereology, and Leprology, Jan.-Feb. 2009, vol. 75, No. 1, pp. 93-96 <DOI:10.4103/0378-6323.45238>.
Saleem, M. et al., "Environment detection and path planning using the e-puck robot", Proceedings of the Masters Erasmus Mundus in Vision and Robotics Meeting Day (Girona, Spain, Jun. 16, 2010), 2010 [retrieved Mar. 8, 2019], pp. 75-81 <vibot.udg.edu/?download=proceedingsVIBOTDay201 O_final.pdf>.
Scarborough, W. et al., "Proposals for ballistocardiographic nomenclature and conventions: revised and extended report of committee on ballistocardiographic terminology", Circulation, Sep. 1956, vol. 14, No. 3, pp. 435-450 <DOI:10.1161/01.CIR.14.3.435>.
Scarborough, W. et al., "The nature of records from ultra-low frequency ballistocardiographic systems and their relation to circulatory events", American Journal of Cardiology, Nov. 1958, vol. 2, No. 5, pp. 613-641 <DOI:10.1016/0002-9149(58)90188-7>.
Scharf, J. et al., "Optimization of portable pulse oximetry through Fourier analysis", 1993 Proceedings of the Twelfth Southern Biomedical Engineering Conference (New Orleans, LA, Apr. 2-4, 1993), 1993, pp. 233-235 <DOI:10.1109/SBEC.1993.247420>.
Scharf, J. et al., "Pulse oximetry through spectral analysis", 1993 Proceedings of the Twelfth Southern Biomedical Engineering Conference (New Orleans, LA, Apr. 2-4, 1993), 1993, pp. 227-229 <DOI:10.1109/SBEC.1993.247418>.
Scully, C. et al., "Physiological parameter monitoring from optical recordings with a mobile phone", IEEE Transactions on Biomedical Engineering, Feb. 2012 (available online Jul. 2011), vol. 59, No. 2, pp. 303-306 <DOI:10.1109/TBME.2011.2163157>.
Shaltis, P. et al., "Cuffless blood pressure monitoring using hydrostatic pressure changes", IEEE Transactions on Biomedical Engineering, Jun. 2008 (Date of Publication: May 2008), vol. 55, No. 6, pp. 1775-1777 <DOI:10.1109/TBME.2008.919142>.
Shao, D. et al., "Monitoring Physiological Signals Using Camera", Arizona State University, PhD Dissertation, Dec. 2016 [retrieved Mar. 1, 2019], 108 pages, retrieved from the internet: <https://repository.asu.edu/items/41236>.
Shao, D. et al., "Noncontact monitoring breathing pattern, exhalation, flow rate and pulse transit time", IEEE Transactions on Biomedical Engineering, Nov. 2014 (Date of Publication: Jun. 2014), vol. 61, No. 11, pp. 2760-2767 <DOI:10.1109/TBME.2014.2327024>.
Shao, D. et al., "Noncontact monitoring of blood oxygen saturation using camera and dual-wavelength imaging system", IEEE Transactions on Biomedical Engineering, Jun. 2016 (Date of Publication: Sep. 2015), vol. 63, No. 6, pp. 1091-1098 <DOI:10.1109/TBME.2015.2481896>.
Shao, D. et al., "Simultaneous Monitoring of Ballistocardiogram and Photoplethysmogram Using Camera", IEEE Transactions of Biomedical Engineering, May 2017 (Date of Publication: Jun. 2016), pp. 1003-1010 <DOI:10.1109/TBME.2016.2585109>.

Sherwood, L., "The Blood Vessels and Blood Pressure", in: Sherwood, L., "Human Physiology: From Cells to Systems" (Cengage Learning, Jan. 2012), pp. 343-388.
Shi, J. et al., "Good features to track", 1994 IEEE Conference on Computer Vision and Pattern Recognition (Seattle, WA, Jun. 21-23, 1994), 1994 (Date Added to IEEE Xplore: Aug. 2002), pp. 593-600 <DOI:10.1109/CVPR.1994.323794>.
Shin, J. et al., "HRV analysis and blood pressure monitoring on weighing scale using BCG", 34th Annual International Conference of the IEEE EMBS (San Diego, CA, Aug. 28-Sep. 1, 2012), 2012 (Date Added to IEEE Xplore: (Nov. 2012), pp. 3789-3792 <DOI:10.1109/EMBC.2012.6346792>.
Shin, J. et al., "Non-constrained monitoring of systolic blood pressure on a weighing scale", Physiological Measurement, Jul. 2009, vol. 30, No. 7, pp. 679-693 <DOI:10.1088/0967-3334/30/7/011>.
Sološenko, A. et al., "Photoplethysmography-based method for automatic detection of Premature Ventricular Contractions", IEEE Transactions on Biomedical Circuits and Systems, Oct. 2015 (Date of Publication: Oct. 2015), vol. 9, No. 5, pp. 662-669 <DOI:10.1109/TBCAS.2015.2477437>.
Alametsä, J. et al., "Ballistocardiography in sitting and horizontal positions", Physiological Measurement, Aug. 2008, vol. 29, No. 29, pp. 1071-1087 <DOI:10.1088/0967-3334/29/9/006>.
Alametsä, J. et al., "The potential of EMFi sensors in heart activity monitoring", 2nd OpenECG Workshop "Integration of the ECG into the EHR & Interoperability of ECG Device Systems" (Berlin, Germany, Apr. 1-3 2004), 2004, 5 pages.
Allen, J. et al., "Age-related changes in peripheral pulse timing characteristics at the ears, fingers and toes", Journal of Human Hypertension, Oct. 2002, vol. 16, No. 10, pp. 711-717 <DOI:10.1038/sj.jhh.1001478>.
Asada, H. et al., "Towards the development of wearable blood pressure sensors: a photo-plethysmograph approach using conducting polymer actuators", Proceedings of the 2005 IEEE Engineering in Medicine and Biology (Shanghai, China, Sep. 1-4, 2005), 2005 (Date Added to IEEE Xplore: Apr. 2006), pp. 4156-4159 <DOI:10.1109/IEMBS.2005.1615379>.
Azmal, G. et al., "Continuous measurement of oxygen saturation level using photoplethysmography signal", International Conference on Biomedical and Pharmaceutical Engineering 2006 (Singapore, Singapore, Dec. 11-14, 2006), 2006, pp. 504-507.
Babchenko, A. et al., "Increase in pulse transit time to the foot after epidural anaesthesia treatment", Medical and Biological Engineering and computing, Nov. 2000, vol. 38, No. 6, pp. 674-679 <DOI:10.1007/BF02344874>.
Baheti, P. et al., "An ultra low power pulse oximeter sensor based on compressed sensing", 6th International Workshop on Wearable and Implantable Body Sensor Networks (Berkeley, CA, Jun. 3-5, 2009), 2009, pp. 144-148 <DOI:10.1109/BSN.2009.32>.
Bal, U. et al., "Non-contact estimation of heart rate and oxygen saturation using ambient light", Biomedical Optics Express, Dec. 2014, vol. 6, No. 1, pp. 86-97 <DOI:10.1364/BOE.6.000086>.
Balakrishnan, G. et al., "Detecting pulse from head motions in video", 2013 IEEE Conference on Computer Vision and Pattern Recognition (Portland, OR, Jun. 23-28, 2013), 2013 (Date Added to IEEE Xplore: Oct. 2013), pp. 3430-3437 <DOI:10.1109/CVPR.2013.440>.
Bickler, P. et al., "Effects of skin pigmentation on pulse oximeter accuracy at low saturation", Anesthesiology, Apr. 2005, vol. 102, No. 4, pp. 715-719 <DOI:10.1097/01.sa.0000220759.21523.1a>.
Boutouyrie, P. et al., "Assessment of pulse wave velocity", Artery Research, Dec. 2008, vol. 3, No. 1, pp. 3-8 <DOI:10.1016/j.artres.2008.11.002>.
Bramwell, J. et al., "Velocity of transmission of the pulse-wave and elasticity of arteries", The Lancet, May 1922, vol. 199, No. 5149, pp. 891-892 <DOI:10.1016/S0140-6736(00)95580-6>.
Brands, P. et al., "A noninvasive method to estimate pulse wave velocity in arteries locally by means of ultrasound", Ultrasound in Medicine and Biology, Nov. 1998, vol. 24, No. 9, pp. 1325-1335 <DOI:10.1016/S0301-5629(98)00126-4>.
Brüser, C. et al., "Adaptive beat-to-beat heart rate estimation in ballistocardiograms", IEEE Transactions on Information Technol-

(56) References Cited

OTHER PUBLICATIONS ogy in Biomedicine, Sep. 2011 (Date of Publication: Mar. 2011), vol. 15, No. 5, pp. 778-786 <DOI:10.1109/TITB.2011.2128337>.

Chandrasekaran, V., "Measuring Vital Signs Using Smart Phones", University of North Texas, Master's Thesis, Dec. 2010 [retrieved Feb. 1, 2019], 130 pages, retrieved from the internet: <https://digital.library.unt.edu/ark:/67531/metadc33139/>.

Chen, Z. et al., "Noninvasive monitoring of blood pressure using optical Ballistocardiography and Photoplethysmograph approaches", 35th Annual International Conference of the IEEE EMBS (Osaka, Japan, Jul. 3-7, 2013), 2013 (Date Added to IEEE Xplore: Sep. 2013), pp. 2425-2428 <DOI:10.1109/EMBC.2013.6610029>.

Coppola, R. et al., "Signal to noise ratio and response variablity measurements in single trial evoked potentials", Electroencephalography and Clinical Neurophysiology, Feb. 1978, vol. 44, No. 2, pp. 214-222 <DOI:10.1016/0013-4694(78)90267-5>.

Corral Martinez, L. et al., "Optimal wavelength selection for noncontact reflection photoplethysmography", Proceedings of 22nd Congress of the International Commission for Optics (Puebla, Mexico, Nov. 2, 2011), 2011, pp. 801191 <DOI:10.1117/12.903190>.

De Hann, G. et al., "Robust pulse rate from chrominance-based rPPG", IEEE Transactions of Biomedical Engineering, Oct. 2013 (Date of Publication: Jun. 2013), vol. 60, No. 10, pp. 2878-2886 <DOI:10.1109/TBME.2013.2266196>.

Edwards Lifesciences, "Understanding Continuous Mixed Venous Oxygen Saturation (SvO2) Monitoring with the Swan-Ganz Oximetry TD System", Edwards Lifesciences, 2002.

Elliot, R. et al., "Acceleration ballistocardiography design, construction, and application of a new instrument", Circulation, Feb. 1954, vol. 9, No. 2, pp. 281-291 <DOI:10.1161/01.CIR.9.2.281>.

Etemadi, M. et al., "Rapid assessment of cardia contractility on a home bathroom scale", IEEE Transactions on Information Technology in Biomedicine, Nov. 2011 (Date of Publication: Aug. 2011), vol. 15, No. 6, pp. 864-869 <DOI:10.1109/TITB.2011.2161998>.

Feng, L. et al., "Motion-Resistant Remote Imaging Photoplethysmography Based on the Optical Properties of Skin", IEEE Transactions on Circuits and Systems for Video Technology, May 2015 (Date of Publication: Oct. 2014), vol. 25, No. 5, pp. 879-891 <DOI:10.1109/TCSVT.2014.2364415>.

Fine, I. et al., "Multiple scattering effect in transmission pulse oximetry", Medical and Biological Engineering and Computing, Sep. 1995, vol. 33, No. 5, pp. 709-712 <DOI:10.1007/BF02441988>.

Freitas, U. et al., "Remote Camera-based Pulse Oximetry", Proceedings of the Sixth International Conference on eHealth, telemedicine, and Social Medicine (Barcelona, Spain, Mar. 23-27, 2014), 2014, pp. 59-63.

Garbey, M. et al., "Contact-free measurement of cardiac pulse based on the analysis of thermal imagery", IEEE Transactions on Biomedical Engineering, Aug. 2007 (Date of Publication: Jul. 2007), vol. 54, No. 8, pp. 1418-1426 <DOI:10.1109/TBME.2007.891930>.

Gesche, H. et al., "Continuous blood pressure measurement by using the pulse transit time: comparison to a cuff-based method", European Journal of Applied Physiology, Jan. 2012, vol. 112, No. 1, pp. 309-315 <DOI:10.1007/s00421-011-1983-3>.

Giovangrandi, L. et al., "Ballistocardiography—a method worth revisiting", 33rd Annual International Conference of the IEEE EMBS (Boston, MA, Aug. 30-Sep. 3, 2011), 2011 (Date Added to IEEE Xplore: Dec. 2011), pp. 4279-4282 <DOI:10.1109/IEMBS.2011.6091062>.

Goedhard, W., "Ballistocardiography: past, present and future", Bibliotheca Cardiologica, Jan. 1979, vol. 37, pp. 27-45.

He, D. et al., "A continuous, wearable, and wireless heart monitor using head ballistocardiogram (BCG) and head electrocardiogram (ECG)", 33rd Annual International Conference of the IEEE EMBS (Boston, MA, Aug. 30-Sep. 3, 2011), 2011 (Date Added to IEEE Xplore: Dec. 2011), pp. 4729-4732 <DOI:10.1109/IEMBS.2011.6091171>.

He, D. et al., "A wearable heart monitor at the ear using ballistocardiogram (BCG) and electrocardiogram (ECG) with a nanowatt ECG heartbeat detection circuit", Massachusetts Institute of Technology, PhD Thesis, Feb. 2013 [retrieved Mar. 1, 2019], 137 pages, retrieved from the internet: <https://dspace.mit.edu/handle/1721.1/79221>.

He, D. et al., "An ear-worn vital signs monitor", IEEE Transactions on Biomedical Engineering, Oct. 2015 (Date of Publication: Jul. 2015), vol. 62, No. 11, 2547-2552 <DOI:10.1109/TBME.2015.2459061>.

Henderson, Y. et al., "The mass-movements of the circulation as shown by a recoil curve", American Journal of Physiology, Sep. 1905, vol. 14, pp. 287-298 <DOI:10.1152/ajplegacy.1905.14.3.287>.

Hu, S. et al., "Feasibility of imaging photoplethysmography", Proceedings of the 2008 International Conference on BioMedical Engineering and Informatics (Sanya, China, May 27-30, 2008), 2008, pp. 72-75 <DOI:10.1109/BMEI.2008.365>.

Humphreys, K. et al., "A CMOS camera-based pulse oximetry imaging system", Proceedings of the 2005 IEEE Engineering in Medicine and Biology (Shanghai, China, Sep. 1-4, 2005), 2005 (Date Added to IEEE Xplore: Apr. 2006), pp. 3494-3497 <DOI:10.1109/IEMBS.2005.1617232>.

Humphreys, K. et al., "Noncontact simultaneous dual wavelength photoplethysmography: A further step toward noncontact pulse oximetry", Review of Scientific Instruments, Apr. 2007, vol. 78, No. 4, pp. 044304, 7 pages <DOI:10.1063/1.2724789>.

Inan, O. et al., "Robust ballistocardiogram acquisition for home monitoring", Physiological Measurment, Feb. 2009, vol. 30, No. 2, pp. 169-185 <DOI:10.1088/0967-3334/30/2/005>.

Jackson, D. et al., "Ballistocardiographic and angiographic correlation study in idiopathic hypertrophic subaortic stenosis", Bibliotheca Cardiologica, Jan. 1971, vol. 27, pp. 14-20.

Jago, J. et al., "Repeatability of peripheral pulse measurements on ears, fingers and toes using photoelectric plethysmography", Clinical Physics and Physiological Measurement, Nov. 1988, vol. 9, No. 4, pp. 319-329 <DOI:10.1088/0143-0815/9/4/003>.

Jiang, J. et al., "What is the space of spectral sensitivity functions for digital color cameras?", 2013 IEEE Workshop on Applications of Computer Vision (Tampa, FL, Jan. 15-17, 2013), 2013 (Date Added to IEEE Xplore: Mar. 2013), pp. 168-179 <DOI:10.1109/WACV.2013.6475015>.

Jin, S. et al., "A robust image tracker based on phase correlation and fourier-mallin transform", International Conference on Control, Automation and Systems 2008 (Seoul, South Korea, Oct. 14-17, 2008), 2008, pp. 1028-1031 <DOI:10.1109/ICCAS.2008.4694650>.

Johnston, W. et al., "Development of a signal processing library for extraction of SpO2, HR, HRV, and RR from photoplethysmographic waveforms", Worcester Polytechnic Institute, Master's Thesis, Jul. 2006 [retrieved Mar. 1, 2019], 147 pages, retrieved from the internet: <https://web.wpi.edu/Pubs/ETD/Available/etd-073106-130906/>.

Kamat, V., "Pulse oximetry", Indian Journal of Anaesthesia, Aug. 2002, vol. 46, No. 4, pp. 261-268.

Kim, C. et al., "Ballistocardiogram as Proximal Timing Reference for Pulse Transit Time Measurement: Potential for Cuffless Blood Pressure Monitoring", IEEE Transactions of Biomedical Engineering, Nov. 2015 (Date of Publication: Jun. 2015), vol. 62, No. 11, pp. 2657-2664 <DOI:10.1109/TBME.2015.2440291>.

Kim, J. et al., "Signal processing using Fourier and wavelet transform for pulse oximetry", 4th Pacific Rim Conference on Lasers and Electro-Optics (Chiba, Japan, Jul. 15-19, 2001), 2001, vol. 2, pp. 310-311 <DOI:10.1109/CLEOPR.2001.970957>.

Kong, L. et al., "Non-contact detection of oxygen saturation based on visible light imaging device using ambient light", Optics Express, Jul. 2013, vol. 21, No. 15, pp. 17464-17471 <DOI:10.1364/OE.21.017464>.

Krug, J. et al., "Optical ballistocardiography for gating and patient monitoring during MRI: an initial study", Computing in Cardiology (Cambridge, MA, Sep. 7-10, 2014), 2014, pp. 953-956.

Kwon, S. et al., "Validation of heart rate extraction using video imaging on a built-in camera system of a smartphone", Proceedings

(56) References Cited

OTHER PUBLICATIONS of the 2012 IEEE Engineering in Medicine and Biology (Seoul, South Korea, Aug. 28-Sep. 1, 2012), 2012 (Date Added to IEEE Xplore: Nov. 2012), pp. 2174-2177 <DOI:10.1109/EMBC.2012.6346392>.
Langewouters, K. et al., "The static elastic properties of 45 human thoracic and 20 abdominal aortas in vitro and the parameters of a new model", Journal of Biomechanics, 1984, vol. 17, No. 6, pp. 425-435 <DOI:10.1016/0021-9290(84)90034-4>.
Lee, J. et al., "Comparison between red, green and blue light reflection photoplethysmography for heart rate monitoring during motion", 35th Annual International Conference of the IEEE EMBS (Osaka, Japan, Jul. 3-7, 2013), 2013 (Date Added to IEEE Xplore: Sep. 2013), pp. 1724-1727 <DOI:10.1109/EMBC.2013.6609852>.
Starr, I. et al., "Ballistocardiogram. II. Normal standards, abnormalities commonly found in diseases of the heart and circulation, and their significance", The Journal of Clinical Investigation, May 1940, vol. 19, No. 3, pp. 437-450 <DOI:10.1172/JCI101145>.
Starr, I. et al., "Studies on the estimation of cardiac output in man, and of abnormalities in cardiac function, from the heart's recoil and the blood's impacts: the ballistocardiogram", American Journal of Physiology, Aug. 1939, vol. 127, No. 1, pp. 1-28.
Starr, I. et al., "Twenty-year studies with the Ballistocardiograph", Circulation, May 1961, vol. 23, No. 5 pp. 714-732 <DOI:10.1161/01.CIR.23.5.714>.
Starr, I., "Essay on the ballistocardiogram", Journal of the American Medical Association, Aug. 1954, vol. 155, No. 16, pp. 1413-1425 <DOI:10.1001/jama.1954.73690340011009>.
Starr, I., "Normal standards for amplitude of ballistocardiograms calibrated by force", Circulation, Jun. 1955, vol. 11, No. 6, pp. 914-926 <DOI:10.1161/01.CIR.11.6.914>.
Starr, I., "On reading ballistocardiograms", American Journal of Cardiology, Oct. 1958, vol. 2, No. 4, pp. 404-416 <DOI:10.1016/0002-9149(58)90326-6>.
Starr, I., "Progress towards a physiological cardiology: a second essay on the ballistocardiogram", Annals of Internal Medicine, Dec. 1965, vol. 63, No. 6, pp. 1079-1105 <DOI:10.7326/0003-4819-63-6-1079>.
Suhatril, R. et al., "Recognition of object categories in realistic scenes", Proceedings of the Masters Erasmus Mundus in Vision and Robotics Meeting Day (Girona, Spain, Jun. 16, 2010), 2010 [retrieved Mar. 8, 2019], pp. 63-68 <vibot.udg.edu/?download=proceedingsVIBOTDay201 O_final.pdf>.
Sun, Y. et al., "Motion-compensated noncontact imaging photoplethysmography to monitor cardiorespitory status during exercise", Journal of Biomedical Optics, Jul. 2011, vol. 16, No. 7, article 077010, 9 pages <DOI:10.1117/1.3602852>.
Sun, Y. et al., "Noncontact imaging photoplethysmography to effectively access pulse rate variability", Journal of Biomedical Optics, Jun. 2013, vol. 18, No. 6 <DOI:10.1117/1.JBO.18.6.061205>.
Takano, C. et al., "Heart rate measurement based on a time-lapse image", Medical Engineering and Physics, Oct. 2007, vol. 29, No. 8, pp. 853-857 <DOI:10.1016/j.medengphy.2006.09.006>.
Tarassenko, L. et al., "Non-contact video-based vital sign monitoring using ambient light and auto-regressive models", Physiological Measurement, Mar. 2014, vol. 35, No. 5, pp. 807-831 <DOI:10.1088/0967-3334/35/5/807>.
Tavakoli, M. et al., "An ultra-low-power pulse oximeter implemented with an energy-efficient transimpedance amplifier", IEEE Transactions on Biomedical Circuits and Systems, Feb. 2010 (Date of Publication: Dec. 2009), vol. 4 No. 1, pp. 27-38 <DOI:10.1109/TBCAS.2009.2033035>.
Thompson, W. et al., "Ballistocardiography. II. The normal ballistocardiogram", Circulation, Mar. 1953, vol. 7, No. 3, pp. 321-328 <DOI:10.1161/01.CIR.7.3.321>.
Tomasi, C. et al., "Detection and tracking of point features", Technical Report CMU-CS-91-132, part 3, 1991, Carnegie Mellon University, 20 pages.
Tsai, H-Y. et al., "A Noncontact Skin Oxygen-Saturation Imaging System for Measuring Human Tissue Oxygen Saturation", IEEE Transactions on Intrumentation and Measurement, Nov. 2014 (Date of Publication: Apr. 2014), vol. 63, No. 11, pp. 2620-2631 <DOI:10.1109/TIM.2014.2312512>.
Tsai, H-Y. et al., "A study on oxygen saturation images constructed from the skin tissue of human hand", 2013 IEEE International Instrumentation and Measurement Technology Conference (Minneapolis, MN, May 6-9, 2013), 2013 (Date Added to IEEE Xplore: Jul. 2013), pp. 58-62 <DOI:10.1109/I2MTC.2013.6555381>.
Tungjitkusolmun, S., "Accuracy and Errors", in: Webster, J. (ed.), "Design of Pulse Oximeters" (Bristol and Phildelphia, Institute of Physics Publishing, 1997), pp. 180-181.
Van Brummelen, A. et al., "On the elimination of pulse wave velocity in stroke volume determination from the ultralow-frequency displacement ballistocardiogram", American Heart Journal, Mar. 1964, vol. 67, No. 3, pp. 374-378 <DOI:10.1016/0002-8703(64)90011-0>.
Verkruysse, W. et al., "Remote plethysmographic imaging using ambient light", Optics Express, Dec. 2008, vol. 16, No. 26, pp. 21434-21445 <DOI:10.1364/OE.16.021434>.
Wang, W. et al., "Exploiting spatial-redundancy of image sensor for motion robust rPPG", IEEE Transactions on Biomedical Engineering, Feb. 2015 (Date of Publication: Sep. 2014), vol. 62, No. 2, pp. 415-425 <DOI:10.1109/TBME.2014.2356291>.
Wieben, O., "Light Absorbance in Pulse Oximetry", in: Webster, J. (ed.), "Design of Pulse Oximeters" (Bristol and Phildelphia, Institute of Physics Publishing, 1997), pp. 52-55.
Wieringa, F. et al., "Contactless multiple wavelength photoplethysmographic imaging: a first step toward 'SpO2 camera' technology", Annals of Biomedical Engineering, Aug. 2005, vol. 33, No. 8, pp. 1034-1041 <DOI:10.1007/s10439-005-5763-2>.
Winokur, E. et al., "A wearable vital signs monitor at the ear for continuous heart rate and Pulse Transit Time measurements", 34th Annual International Conference of the IEEE EMBS (San Diego, CA, Aug. 28-Sep. 1, 2012), 2012 (Date Added to IEEE Xplore: Nov. 2012), pp. 2724-2727 <DOI:10.1109/EMBC.2012.6346527>.
Withings Inc., "What does SpO2 mean? What is the normal blood oxygen level?" [online], Withings Inc., Mar. 2015 [retrieved on Mar. 11, 2019 from archive.org, as it appeared on Apr. 14, 2015], retrieved from the internet: <URL: https://web.archive.org/web/20150414234712/https://withings.zendesk.com/hc/en-us/articles/201494667-What-does-SpO2-mean-What-is-the-normal-blood-oxygen-level->.
Won, B. et al., "A Touchscreen as a Biomolecule Detection Platform", Angewandte Chemie, Jan. 2012 [available online Oct. 2011], vol. 51, No. 3, pp. 748-751 <DOI:10.1002/anie.201105986 >.
Wong, M. et al., "The relationship between pulse transit time and systolic blood pressure on individual subjects after exercises", Proceedings of the 1st Distributed Diagnosis and Home Healthcare (D2H2) Conference (Arlington, VA, Apr. 2-4, 2006), 2006, pp. 37-38 <DOI:10.1109/DDHH.2006.1624791>.
Yu, S. et al., "A Wireless Physiological Signal Monitoring System with Integrated Bluetooth and WiFi Technologies", Proceedings of the 2005 IEEE Engineering in Medicine and Biology (Shanghai, China, Sep. 1-4, 2005), 2005 (Date Added to IEEE Xplore: Apr. 2006), pp. 2203-2206 <DOI:10.1109/IEMBS.2005.1616900>.
Zhao, F. et al., "Remote measurements of heart and respiration rates for telemedicine", PLOS One, Oct. 2013, vol. 8, No. 10, article No. e71384, 14 pages <DOI:10.1371/journal.pone.0071384>.
Zonios, G. et al., "Pulse Oximetry Theory and Calibration for Low Saturations", IEEE Transactions on Biomedical Engineering, May 2004 (Date of Publication: Apr. 2004), vol. 51, No. 5, pp. 818-822 <DOI:10.1109/TBME.2004.826685>.

\* cited by examiner

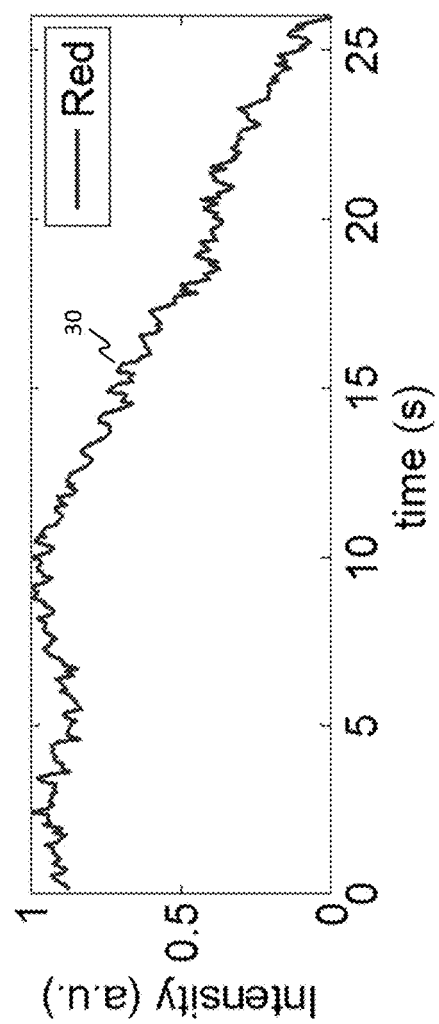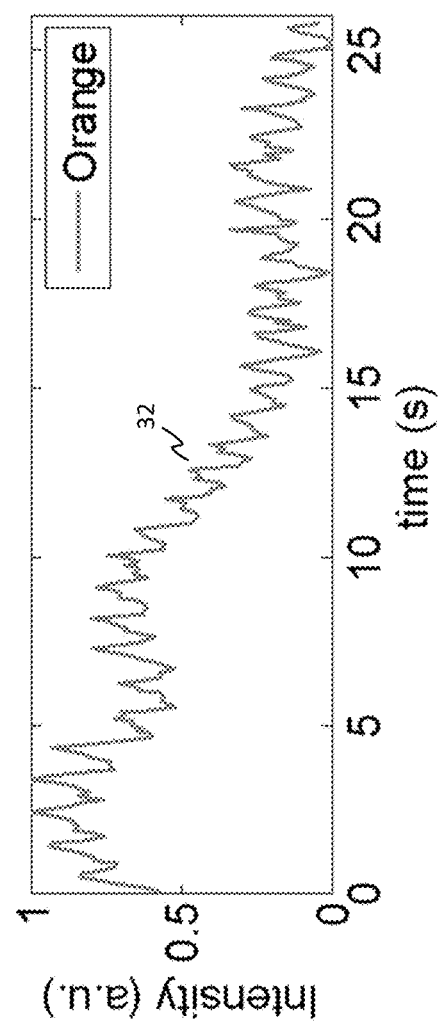

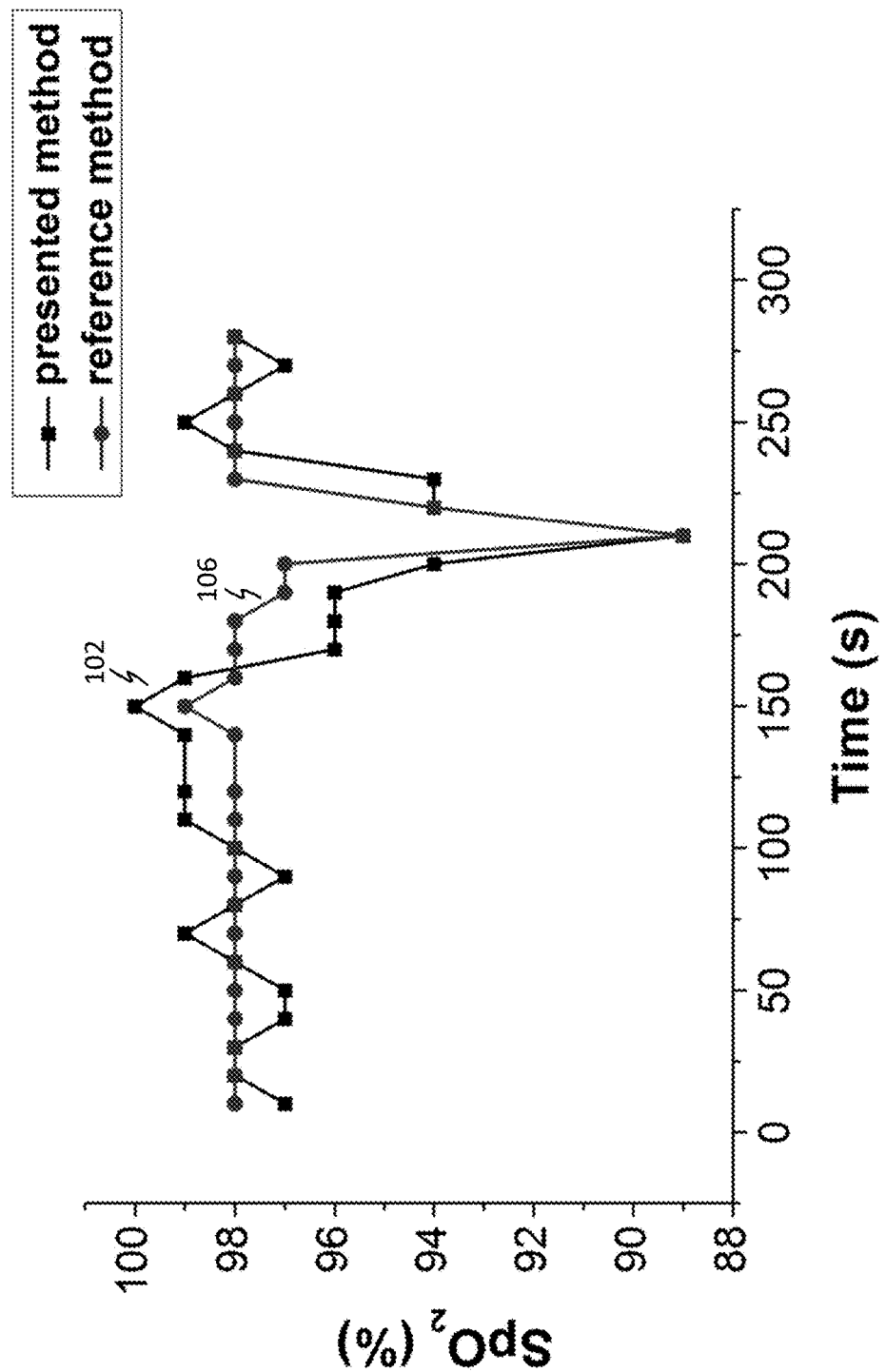

NONCONTACT MONITORING OF BLOOD OXYGEN SATURATION USING CAMERA

RELATED APPLICATION

This application claims priority from U.S. application No. 62/252,949 of Nongjian Tao et al., filed Nov. 9, 2015, entitled "NONCONTACT MONITORING OF BLOOD OXYGEN SATURATION USING CAMERA." U.S. application No. 62/252,949 is hereby incorporated by reference.

TECHNICAL FIELD

The present invention relates to non-contact measurement of blood oxygen saturation ($SpO_2$) in a mammalian subject, and, more particularly to a device having a camera, one or more arrays of LEDs emitting near infrared (NIR) and orange light, and a controller.

BACKGROUND

Oxygen saturation, along with heart rate, breathing rate, blood pressure, and body temperature, is a vital physiological parameter. It is a relative measure of the oxygen amount dissolved or carried in a given medium, such as blood. It indicates whether a person has sufficient supply of oxygen and reflects the health level of the cardiorespiratory system. Continuous monitoring of oxygen saturation level is important in detecting hypoxemia under many medical situations, including anesthesia, sleep apnea, and parturition. It is employed in intensive care, operating room, emergency care, neonatal care, sleep study, and veterinary care [1].

Mixed venous oxygen saturation ($SvO_2$), tissue oxygen saturation ($StO_2$), and arterial oxygen saturation ($SaO_2$) are a few major methods used for the determination of oxygen saturation levels in human body. $SvO_2$ is a measurement of the oxygen remaining in the blood after passing through the capillary bed, which indicates moment-to-moment variation between oxygen supply and demand [2]. It can be monitored using fiber optics catheters. $StO_2$ provides an assessment of tissue perfusion and it can be measured by near infrared (NIR) spectroscopy. $SaO_2$ is a measurement of oxygen saturation in the arteries. An estimation of $SaO_2$ at peripheral capillary is called $SpO_2$, which is the primary focus of this paper. Unlike traditional $SaO_2$ measurement, which is normally conducted invasively via a blood test with a blood gas analyzer, $SpO_2$ can be measured by noninvasive methods. Monitoring $SpO_2$ provides a quick and convenient assessment of user's oxygenation status. The most widely used device for $SpO_2$ monitoring is pulse oximeter, which is often attached to the finger for measurement purpose. The hardware implementation of pulse oximetry includes two main components: 1) an illumination source usually composed of a dual-wavelength LED, and 2) a photodetector—typically a photodiode. $SpO_2$ values typically range from 95% to 100% in healthy individuals. Continuous low $SpO_2$ levels (<90%) may indicate an oxygen delivery problem [3].

Recent technological advances have enabled measurements of some of the physiological signals in noncontact ways [4]-[6]. Remote $SpO_2$ detection provides people with a method to measure oxygen saturation noninvasively under normal daily setting. Absence of physical contact between the subject and the device allows for a more comfortable and less stressful measurement condition. The inaccurate $SpO_2$ readings caused by varied pressure applied from finger to the contact sensor can also be avoided [7], besides preventing skin irritation that can occur in some individuals, especially infants, during extended monitoring periods. Noncontact pulse oximetry also provides a suitable $SpO_2$ measurement alternative for individuals with finger injuries, or for those with poor peripheral perfusion or dark pigmentation on fingers, for whom traditional pulse oximetry may otherwise lead to inaccurate measurements [8].

In recent years, researchers have attempted different $SpO_2$ measurement approaches using noncontact methods. For example, Humphreys et al. [9], [10] used a CMOS camera with LED arrays that emit two different wavelengths as the light source for noncontact pulse oximetry. Due to low frame rate and sensitivity to ambient light, the noise in the measured PPG signals was too large to obtain accurate $SpO_2$ values. Wieringa et al. [11] also used a CMOS camera, but with three different wavelengths to investigate the feasibility of an "$SpO_2$ camera." However, no $SpO_2$ results were presented due to poor SNR of the PPG signals. Kong et al. [12] used two CCD cameras, each mounted with a narrow bandpass filter to capture PPG signals at two different wavelengths (520 and 660 nm) in ambient lighting condition. The test only covered a narrow $SpO_2$ range (97%-99%). For practical applications, such as clinical settings, it is necessary to be able to measure $SpO_2$ over a wider range (at least 80%-100%). Tarassenko et al. [13] and Bal et al. [14] used a camera to calculate $SpO_2$ based on the PPG information obtained from the RGB channels under ambient lighting condition. Other researchers have found that the PPG signals extracted from the red and blue channels were noisier than those extracted from the green channel [6], [15], [16]. Moreover, for digital cameras, each color channel (red, green, or blue) covers a band of optical spectrum [17] with a width of ~100 nm, which is different from the traditional pulse oximetry method that uses monochromatic light sources with wavelengths selected to maximize the detection sensitivity of oxygenated and deoxygenated hemoglobin in blood. Tsai et al. [18], [19] used a CCD camera with red and infrared LEDs to take still images of hand and analyzed $SpO_2$ by looking into the reflective intensity of the shallow skin tissue. These authors compared the $SpO_2$ results against partial pressure of oxygen values ($PaO_2$), instead of the standard pulse oximetry. Although they showed correlation between the results obtained using the two methods, a direct demonstration of $SpO_2$ measurement is still lacking.

The present invention, in contrast to the above discussed methods, is a new noncontact method which is based on video recording of a subject's facial area to measure $SpO_2$. To the best of the inventors' knowledge, this is the first demonstration of a low-cost video-based method with high temporal resolution and signal-to-noise ratio to accurately monitor wide range of $SpO_2$ without any physical contact between the subject and the device. The contributions of this study include: 1) development of a hardware system with video capture and illumination synchronization control, 2) identification of optimized light sources to achieve accurate PPG and $SpO_2$ detection when using noncontact method, 3) validation of method over a wide clinically relevant range of $SpO_2$ via a pilot study of subjects, and 4) addition of $SpO_2$ tracking to our previously reported noncontact physiological monitoring platform, which can detect heart rate, breathing pattern, and pulse transit time [4].

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

Disclosed herein is device for non-contact measurement of blood oxygen saturation ($SpO_2$) in a mammalian subject including a camera and one or more arrays of LEDs each having a first set of LEDs emitting near infrared (NIR), and the second set of LEDs emitting orange light located in an optical path adapted to transmit reflected light from a subject to the camera. A controller transmits a camera trigger to the camera, and is further coupled to transmit control signals to the one or more arrays of LEDs. A processor receives photoplethysmography (PPG) data signal values from the camera. The PPG data signal values are present in the reflected light and include pulsatile and non-pulsatile components. The processor determines $SpO_2$ values from the PPG data signal values from the measured ratios of pulsatile to non-pulsatile components of the PPG signals.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIG. 2A shows PPG signals measured simultaneously using the camera with red ($\lambda$=660 nm) LEDs.

FIG. 2B shows PPG signals measured simultaneously using the camera with orange ($\lambda$=611 nm) LEDs.

FIG. 10A and FIG. 10B show examples of $SpO_2$ measured using a pulse oximeter (reference method) and using the new method disclosed herein.

Figure 1:
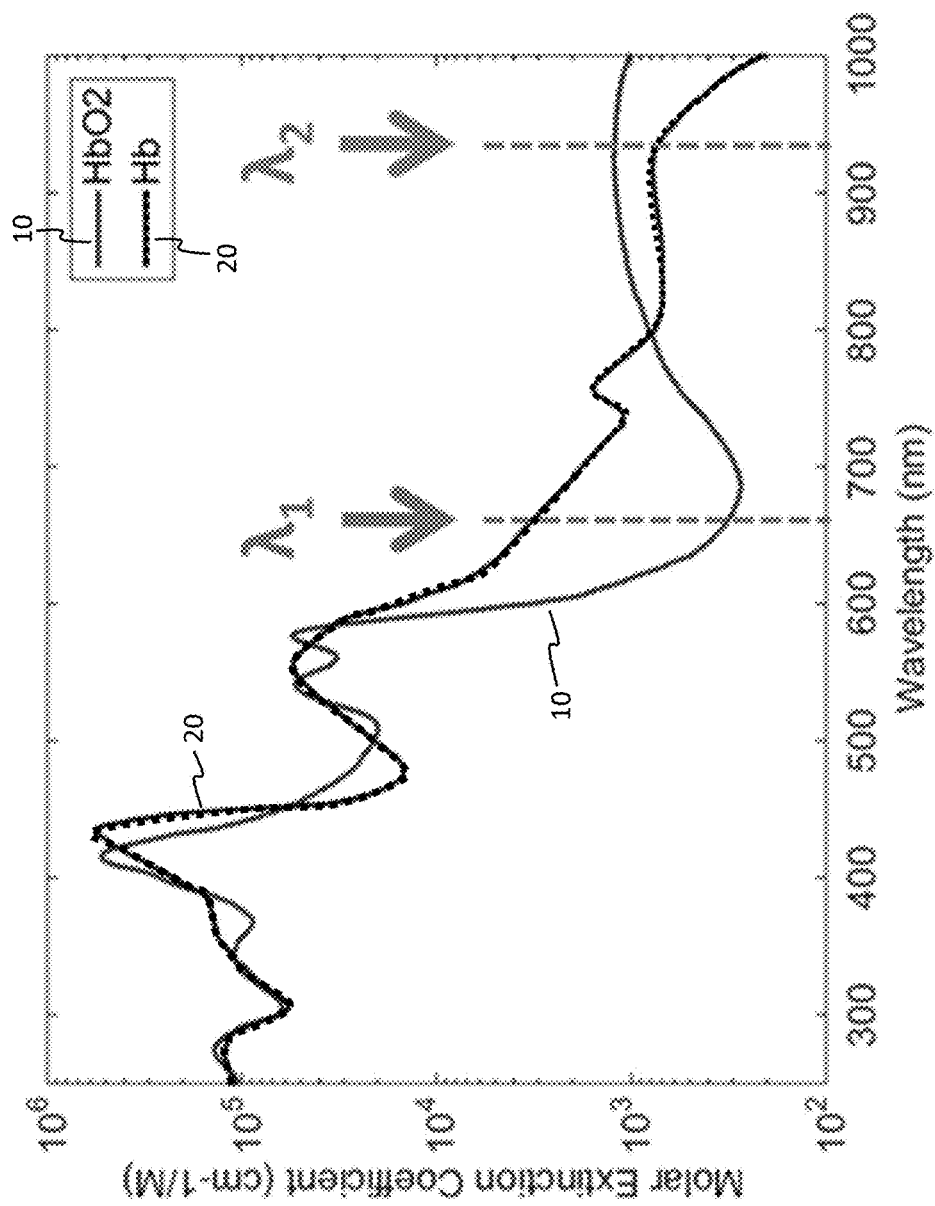
FIG. 1 shows an example of absorption spectra of $HbO_2$ and Hb.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

The following disclosure describes a device for non-contact measurement of blood oxygen saturation ($SpO_2$). Several features of methods and systems in accordance with example embodiments are set forth and described in the figures. It will be appreciated that methods and systems in accordance with other example embodiments can include additional procedures or features different than those shown in the figures. Example embodiments are described herein with respect to device for non-contact measurement of blood oxygen saturation ($SpO_2$) including a camera and LED arrays. However, it will be understood that these examples are for the purpose of illustrating the principles, and that the invention is not so limited.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

Generally, as used herein, the following terms have the following meanings when used within the context of microarray technology:

The articles "a" or "an" and the phrase "at least one" as used herein refers to one or more.

As used herein, "plurality" is understood to mean more than one. For example, a plurality refers to at least two, three, four, five, ten, 25, 50, 75, 100, 1,000, 10,000 or more.

As used in this specification, the terms "processor" and "computer processor" encompass a personal computer, a tablet computer, a smart phone, a microcontroller, a microprocessor, a field programmable object array (FPOA), a digital signal processor (DSP), an application-specific integrated circuit (ASIC), a field programmable gate array (FPGA), a programmable logic array (PLA), or any other digital processing engine, device or equivalent capable of executing software code including related memory devices, transmission devices, pointing devices, input/output devices, displays and equivalents.

"Obtaining" is understood herein as manufacturing, purchasing, or otherwise coming into possession of.

"PPG" refers to photoplethysmography signals.

"ROI" refers to region of interest.

"RR" refers to RR, ratio of ratios, refers to the ratio of absorbance at two wavelengths (λ1 and λ2).

"SNR" refers to signal-to-noise ratio.

"SpO$_2$" refers to peripheral capillary oxygen saturation, an estimate of the amount of oxygen in the blood.

Example Embodiments

Referring now to FIG. 1, an example of SpO$_2$ measurement using a dual-wavelength imaging system is shown. SpO$_2$ is the percentage of oxygenated hemoglobin at peripheral capillary and can be expressed by the following equation, $$SpO_2 = \frac{[HbO_2]}{[HbO_2] + [Hb]} \times 100\%. \quad (1)$$

where [HbO$_2$], plot 10, is the concentration of oxygenated hemoglobin and [Hb], plot 20, is the concentration of deoxygenated hemoglobin.

Traditional pulse oximetry measures SpO$_2$ based on the differential absorption of light by HbO$_2$ and Hb at two wavelengths. Depending upon the optical absorption spectrum of HbO$_2$ and Hb shown, it is possible to select two wavelengths, $\lambda_1$ and $\lambda_2$, such that absorbance by HbO$_2$ is more at $\lambda_2$ than at $\lambda_1$, while the absorbance by Hb is more at $\lambda_1$ than at $\lambda_2$.

The Beer-Lambert law—widely used to determine a solution's configuration by optical transmittance measurement—states that light absorption by a substance in a solution is proportional to its concentration [21]. Pulse oximetry assumes that the pulsatile component (AC) of optical absorption originates from the pulsatile arterial blood, and the non-pulsatile component (DC) contains contributions from non-pulsatile arterial blood, venous blood, and other tissues. The pulsatile signals (AC) can be normalized by the non-pulsatile signals (DC) at λ1 and λ2, to give the pulsatile absorbance rates as follows, $$R_{\lambda_1} = \frac{AC_{\lambda_1}}{DC_{\lambda_1}}. \quad (2)$$

$$R_{\lambda_2} = \frac{AC_{\lambda_2}}{DC_{\lambda_2}}. \quad (3)$$

The ratio of absorbance at two wavelengths is defined as ratio of ratios, RR, $$RR = \frac{R_{\lambda_1}}{R_{\lambda_2}} = \frac{AC_{\lambda_1}/DC_{\lambda_1}}{AC_{\lambda_2}/DC_{\lambda_2}}. \quad (4)$$

RR can be regarded as nearly linear with respect to SpO$_2$ [12], [14], [22], $$SpO_2 = k \times RR + b \quad (5)$$

where k and b are linear equation coefficients. Thus, SpO$_2$ value can be obtained by measuring RR. This dual-wavelength ratio method provides an easy way to determine SpO$_2$, and the result is independent of both light path length and concentration of blood constituents that absorb light.

The presently disclosed method of SpO$_2$ detection is based on optical principles similar to traditional pulse oximetry. A key difference is the ability to track SpO$_2$ change using a noncontact method based on the reflected light as disclosed herein.

As mentioned above, SpO$_2$ detection using the RR value requires employing at least two wavelengths. For accurate measurement, it is preferable that 1) the measured PPG signals have high SNR at both wavelengths, and 2) optical absorption associated with HbO$_2$ is opposite to that associated with Hb, and the differences between them are large at the two wavelengths, as shown in FIG. 1.

Traditional contact-based pulse oximetry uses a dual-wavelength LED at red (λ=660 nm) and near infrared (NIR) (λ=940 nm) wavelengths as light source, and a photodiode as light detector. For transmission-mode pulse oximetry, the LED and photodiode are placed at either sides of the tissue (e.g., finger or earlobe), and for reflection-mode pulse oximetry, the LED and photodiode are positioned on the same side of the tissue. As shown in FIG. 1, the red light 10 at 660 nm is absorbed more by Hb than by HbO$_2$, while the NIR light 20 at 940 nm is absorbed more by HbO$_2$ than by Hb. The 660 and 940 nm wavelength combination produces high-quality data for the contact pulse oximetry, but it is not suitable for the presented noncontact method.

It was observed that the use of red LED at 660 nm for the non-contact method results in poor PPG signal. To find a suitable replacement for the 660-nm LED, we evaluated the noncontact PPG signals at various wavelengths, ranging from 470 to 940 nm, and observed that the best PPG signal is obtained when green light is used, which is consistent with the literature [6], [15], [16]. However, the optical absorption difference between HbO$_2$ and Hb at green is small (see FIG. 1); thereby, making green unsuitable for SpO$_2$ measurement. We ruled out blue because its optical absorption is similar to NIR with high HbO$_2$ absorbance and low Hb absorbance despite the fact that its use produces good-quality PPG signal [23]. We determined orange (λ=590 to 635 nm) to be the most suitable substitute for our application because its optical absorption property fulfills the specified criteria—high Hb and low HbO$_2$ absorbance—and due to the superior PPG signals (shown in FIG. 2A and FIG. 2B) measured via the noncontact method when using orange LED, as compared to red LED. FIG. 2A, shows PPG signals measured simultaneously using the camera with red (λ=660 nm) LEDs. The PPG signals 30 are plotted with intensity in angstrom units (a.u.) on the Y axis and time in seconds on the X axis. Referring now to FIG. 2B shows PPG signals measured simultaneously using the camera with orange (λh=611 nm) LEDs. The PPG signals 32 are plotted with intensity in angstrom units (a.u.) on the Y axis and time in seconds on the X axis.

We also examined the suitability of the 940-nm LED—used in conventional contact pulse oximetry—for our imaging system, and found the PPG signal obtained using it to be unsatisfactory due to low SNR. The primary reason for this was the low quantum efficiency of the CMOS imager at 940 nm. NIR at wavelength 880 nm was found to provide better quality PPG signal obtained using the camera sensor. Moreover, 880 and 940 nm have similar optical absorptions by HbO$_2$ and Hb. These two reasons prompted the use of 880-nm LED, instead of 940-nm LED, in conjunction with the 610-nm orange LED for the presented method.

Performance of the 610-nm orange and 880-nm NIR combination was examined with a simulation of the dependence of RR on SpO$_2$ from 70% to 100%. The simulation was based on the Beer-Lambert law and the assumption that absorption of light in blood is only related to HbO$_2$ and Hb, which lead to the following RR equation:

$$RR = \frac{s \times \varepsilon_{HbO_2\_\lambda_1} + (1-s) \times \varepsilon_{Hb\_\lambda_1}}{s \times \varepsilon_{HbO_2\_\lambda_2} + (1-s) \times \varepsilon_{Hb\_\lambda_2}}. \quad (6)$$

where s is the oxygen saturation (SpO$_2$), and $\varepsilon_{HbO_2\_\lambda_i}$ and $\varepsilon_{Hb\_\lambda_i}$ are the extinction coefficients of HbO$_2$ and Hb at the two wavelengths [21].

Figure 3:
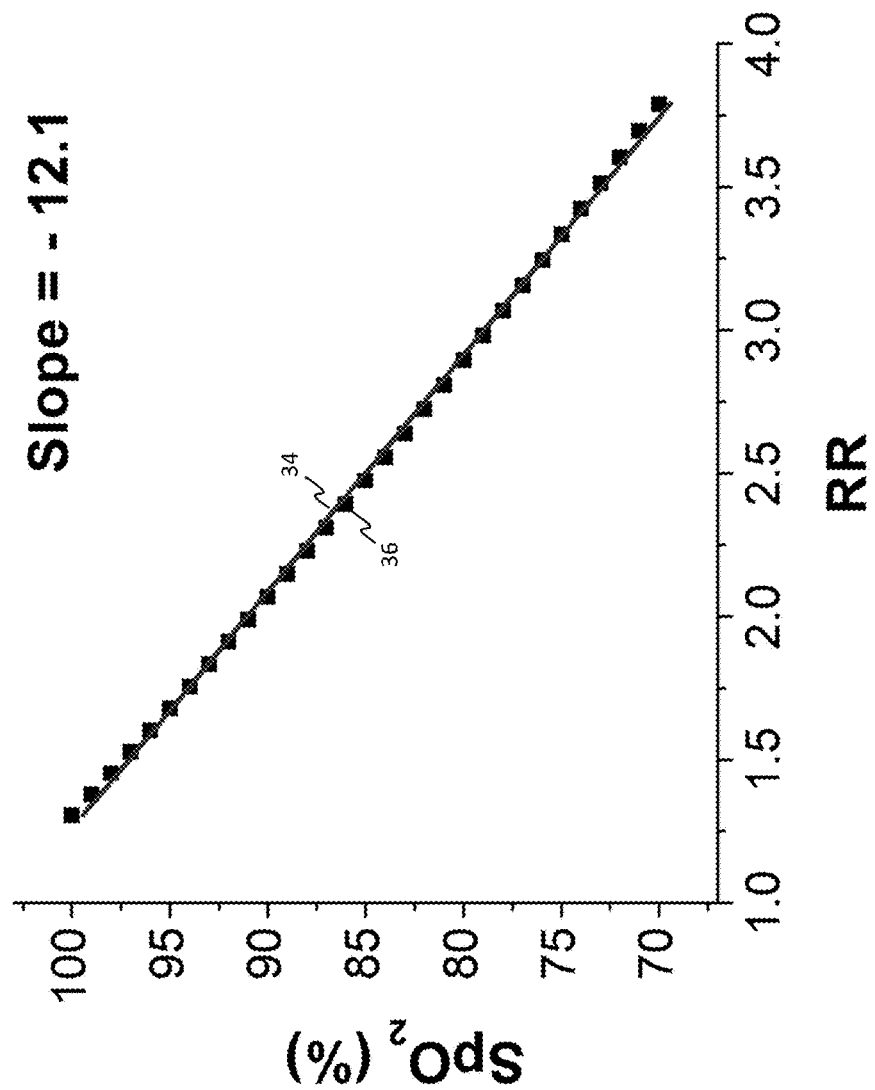
FIG. 3 shows a relationship between $SpO_2$ and RR (with wavelengths at 610 and 880 nm) based on equation (6) using extinction coefficients from [20].

Referring now to FIG. 3, a relationship between SpO$_2$ and RR (with wavelengths at 610 and 880 nm) based on equation (6) using extinction coefficients from [20] is shown. Line 34 is a linear fit for plot points 36. The simulation result indicates that SpO$_2$ is linearly proportional to RR (R$^2$~1) with a maximum error <0.6% over a broad range (70%-100%), and can be approximated by equation (5). The linear relationship is consistent with other studies [12], [14], [22]. Coefficient k in equation (5) can be estimated from the linear fit curve slope, which is −12.1

Figure 4:
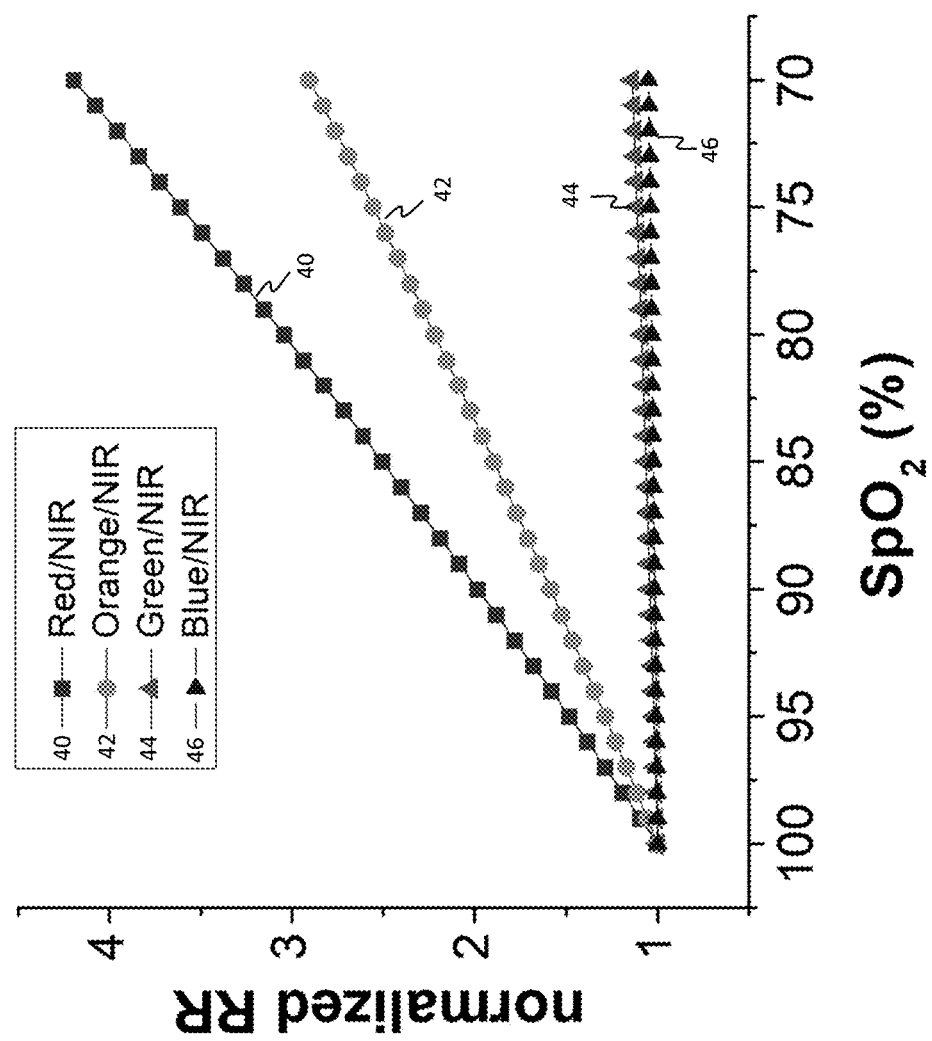
FIG. 4. shows simulated plots of normalized RR versus $SpO_2$ based on four different wavelength combinations.

Referring now to FIG. 4, simulated plots of normalized RR versus SpO$_2$ based on four different wavelength combinations are shown. Similar simulations with different wavelength combinations were carried out to determine the best wavelength combination for accurate SpO$_2$ measurement. A plot of normalized RR on the y-axis is plotted against SpO$_2$ on the X axis where curve 40 represents Red ($\lambda$=660 nm) and NIR ($\lambda$=880 nm), where curve 42 represents Orange ($\lambda$=610 nm) and NIR ($\lambda$=880 nm), where curve 44 represents Green ($\lambda$=528 nm) and NIR ($\lambda$=880 nm). Backspace, and where curve 46 represents Blue ($\lambda$=470 nm) and NIR ($\lambda$=880 nm). The extinction coefficients used are from reference [20].

For easy comparison of results at different wavelength combinations, each plot was normalized by the corresponding RR value at 100% SpO$_2$. The steeper the curve, the more sensitive a combination is to SpO$_2$ change. The red/NIR combination, which is widely used in the traditional pulse oximetry, shows the steepest curve. When SpO$_2$ drops from 100% to 70%, RR changes by 319%, indicating that this combination is most sensitive to SpO$_2$ change. However, for the green/NIR and blue/NIR combinations, RR changes by only 14% and 5%, respectively, indicating their unsuitability to detect SpO$_2$ changes. The orange/NIR combination shows a change of RR by 190%. Although it is not as good as the red/NIR combination, it is the best choice for noncontact SpO$_2$ tracking when the SNRs of the PPG signals are considered.

Hardware Implementation

Figure 5:
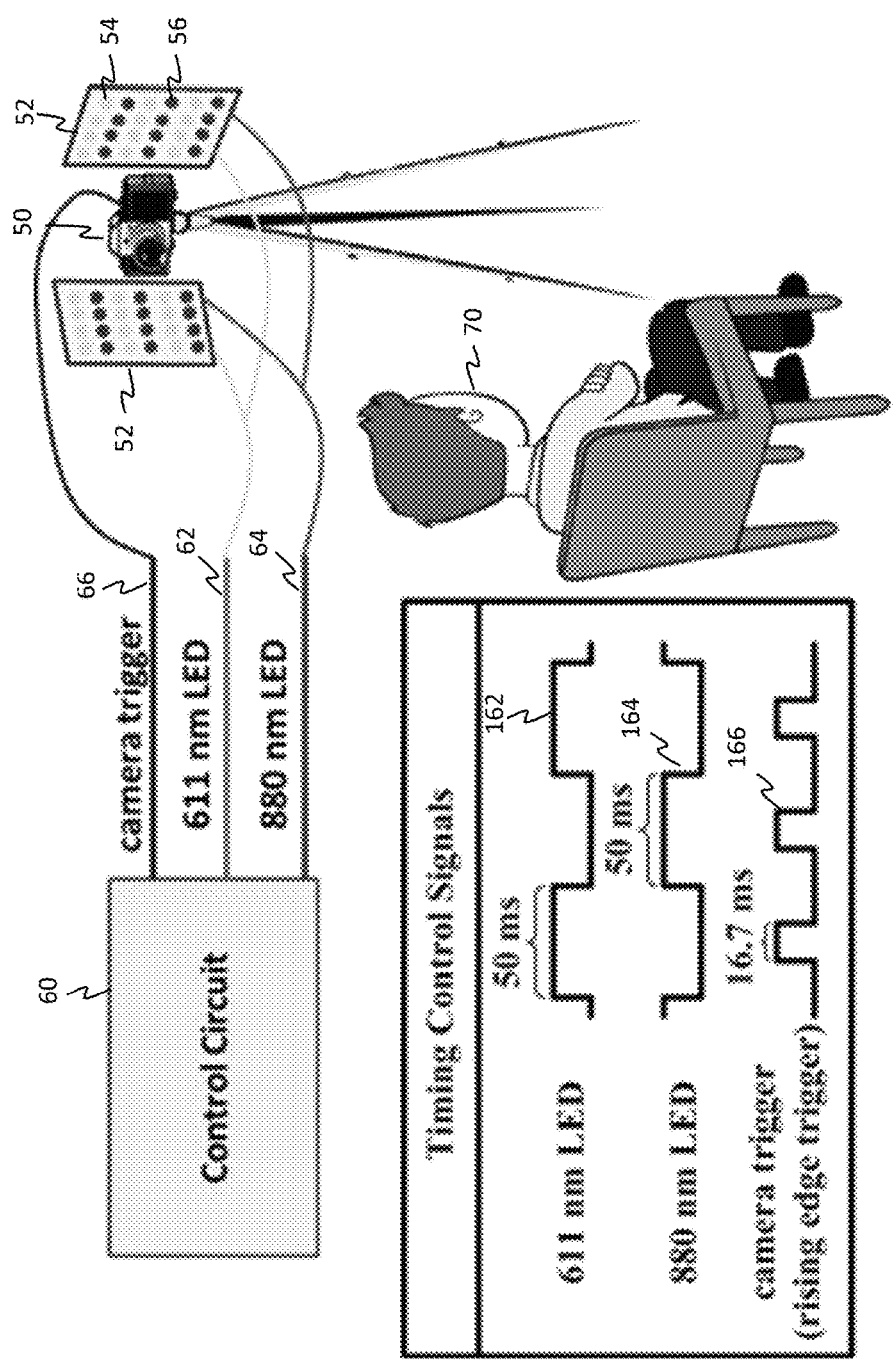
FIG. 5 shows an example of an experimental setup and control signals.

Referring now to FIG. 5, an example of an experimental setup and control signals is shown. The experimental setup includes a PixeLINK monochromatic camera 50, model number PL-B741EU, with a Fujinon HF16HA1B 16-mm f/1.4 fixed focal lens was used to record the videos. The illumination system consisted of two identical LED arrays 52 placed symmetrically on the left and right sides of the camera. Each array included alternating rows of NIR (QED223, Fairchild Semiconductor) 54 and orange (SLI-570DT3F, Rohm Semiconductor) LEDs. A microcontroller (Texas Instruments MSP430F5348) 60 was connected to the camera by camera trigger 66, to the 611 nm LEDs by control line 62, and to the 880 nm LEDs by control line 64. The microcontroller 60 was used to generate LED signals 162, 164 and camera trigger signals 166 to switch the NIR and orange LEDs on and off alternatively so as to capture an image every 50 ms at the camera's trigger signal rising edge when either the NIR or the orange LEDs were on. The camera 50 was triggered 20 times/s, so for each wavelength, the corresponding frame rate was 10 frames/s. All videos were taken indoors without ambient lights to avoid noise caused by ambient lighting.

Experiment Design

Still referring to FIG. 5, subjects 70 were asked to sit still approximately 30 cm from the camera and LED arrays. As long as clear focus and proper size were guaranteed for the region of interest (ROI), the distance did not affect the signal much, which was partially due to ac/dc normalization. A blindfold was used for comfort and eye protection. Each experiment lasted 5 min. The normal SpO$_2$ range is 95%-100% in healthy people. To validate the presented method for low SpO$_2$ (<90%), the subjects were asked to hold their breath until they felt uncomfortable in order for their blood to reach low oxygen saturation level—a technique also used by other researchers [12], [22]. There is no known risk associated with holding breath for 0.5-1.5 min in healthy people. To produce a noticeable drop in SpO$_2$, the subjects must hold their breath for at least 30 s. Notwithstanding this equal time duration, the SpO$_2$ drop observed varied from one individual to another because of the varying lung capacity and hemoglobin oxygenation efficiency. It was noted that after holding breath for 1 min, SpO$_2$ dropped below 90% in some subjects while in others, the drop was much smaller.

The subjects were asked to breathe normally for the first 2 min, during which the SpO$_2$ value was stable due to the sufficient oxygen supply. After this initial 2-min period, each subject was asked to hold breath as long as possible to produce an SpO$_2$ drop. When the subject resumed breathing, SpO$_2$ recovered to the same level as that before holding breath, usually within a few.

SpO$_2$ measurements were also carried out simultaneously using a (not shown) commercial contact pulse oximeter (Homedics PX-100) for comparison. The commercial contact pulse oximeter provided a reading nearly every 10 s.

Data Processing

Figure 6:
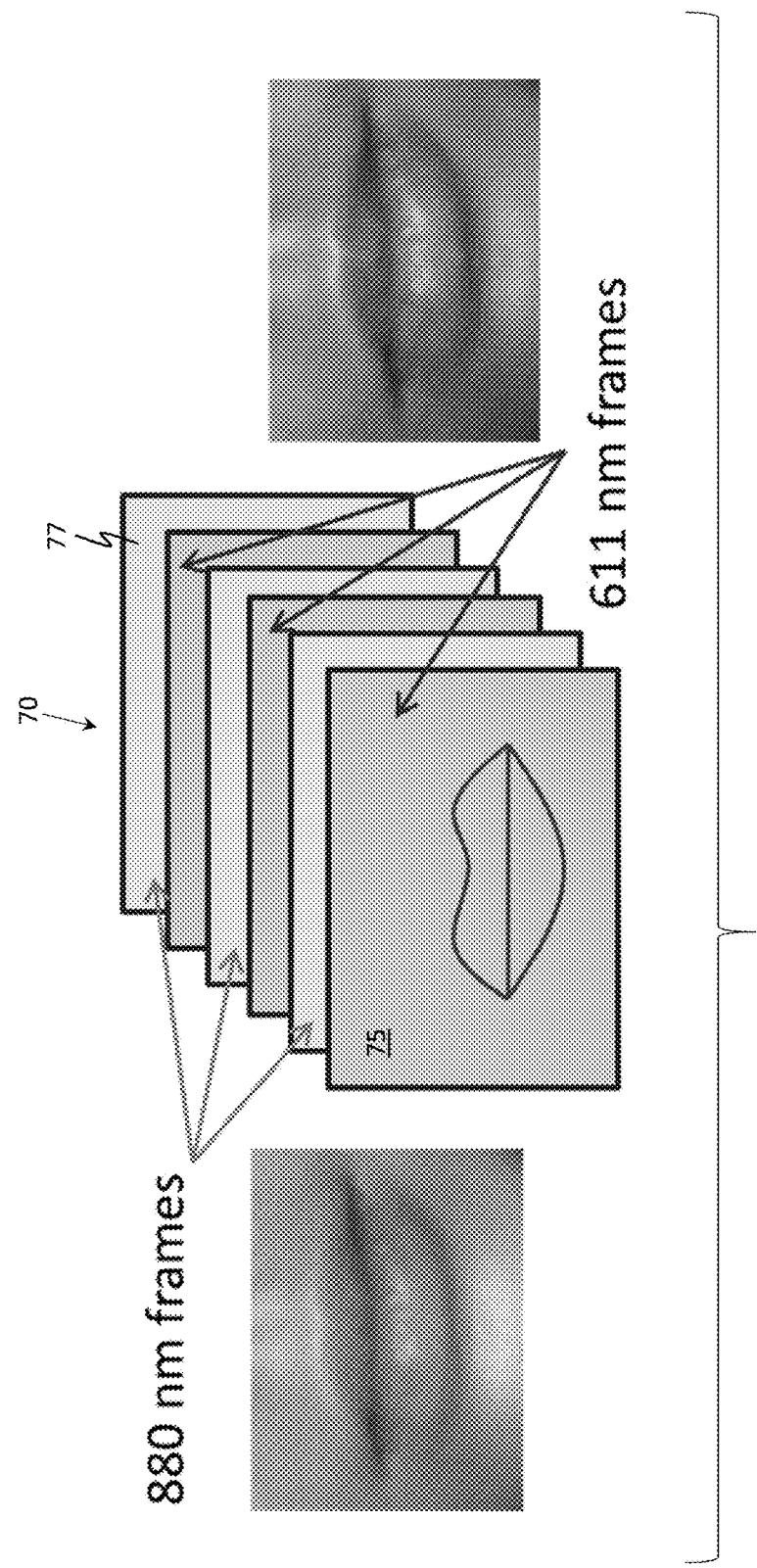
FIG. 6 shows an example of an image sequence acquisition with two different wavelengths.

Now referring to FIG. 6, an example of an image sequence acquisition with two different wavelengths shown. A previous study [4] conducted at Arizona State University has shown that the area around the lips provides a suitable region for good PPG signal measurement. For this reason, an area of 160×120 pixels around the lips was selected as the ROI. After capturing the videos, the ROI was analyzed using the following procedure. The acquired images 70 were sorted into two groups, viz., NIR 77 and orange 75, based on the wavelength at which they were captured. In each group, the image intensity was averaged over all the ROI pixels in every frame to obtain the PPG signal at the corresponding wavelength. Each of the two PPG signals were divided equally into 10-s subsets to provide SpO$_2$ data with a time resolution similar to the commercial contact pulse oximeter that was used as a reference.

Figure 7:
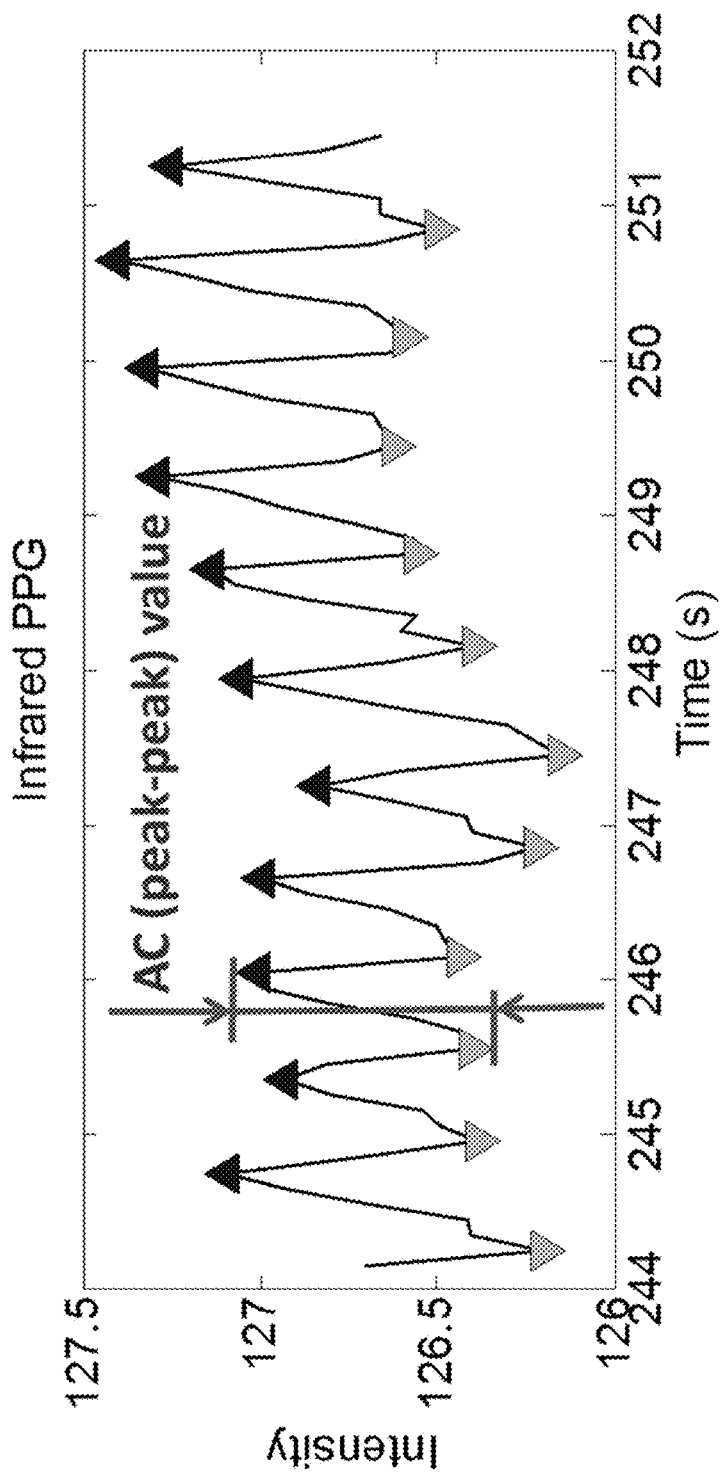
FIG. 7 shows an example of an AC value obtained from PPG signal.

Now referring to FIG. 7, an example of an AC value obtained from PPG signal is shown. For each of the 10-s subsets, the ac and the dc components of the PPG signal were obtained using the average peak-to-peak and mean values, respectively. Fast Fourier transformation (FFT) can also be used to extract the PPG signal ac component [24]-[29], but it works well only when the heart rate remains constant, and yields inaccurate results when heart rate variability is high. The RR values were determined from equation (4) by using the measured ac and the dc PPG signal components. To extract SpO$_2$ from RR, equation (5) was used, where k was determined from the slope of the plot shown in FIG. 3, and the intercept b was determined from the baseline SpO$_2$ level and corresponding average RR value obtained during the initial 2 min of each test.

Validation of the Wavelength Selection

Figure 8C:
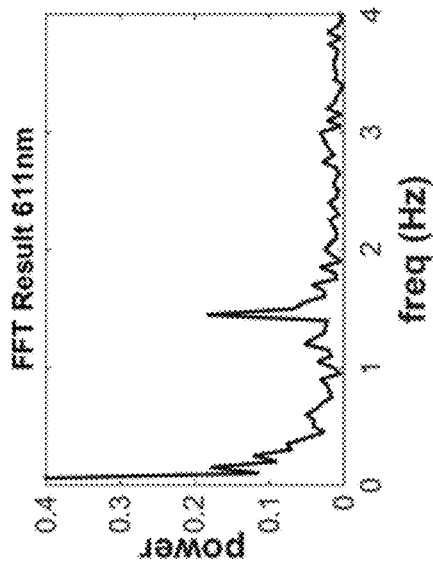
FIG. 8C shows an example of FFT spectra for 611 nm.
Figure 8D:
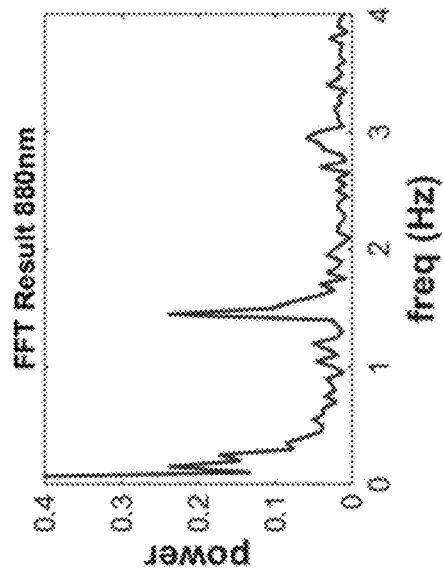
FIG. 8D shows an example of FFT spectra for 880 nm.
Figure 8A:
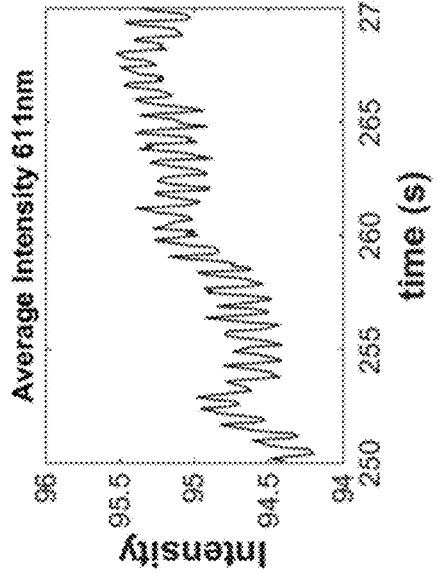
FIG. 8A shows an example of the average intensity of PPG signals obtained at 611 nm.
Figure 8B:
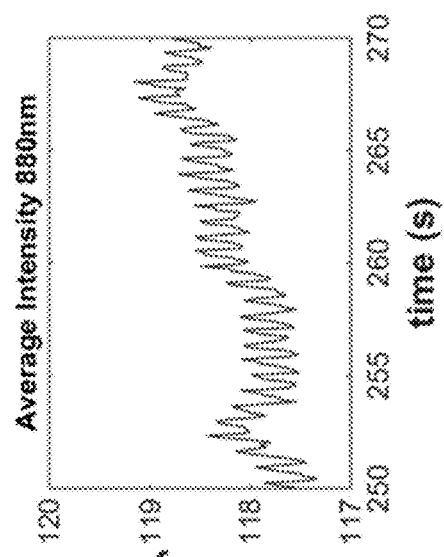
FIG. 8B shows an example of the average intensity of PPG signals obtained at 880 nm.

Now referring simultaneously to FIG. 8A-FIG. 8D examples of the average intensity of PPG signals and corresponding FFT spectra obtained at 611 nm are shown 880 nm in separate plots. The detection of noncontact PPG signals was validated at 611 nm and 880 nm. PPG signals were recorded at the two wavelengths simultaneously, both showing heart beating clearly as plotted FIG. 8A and FIG. 8B. AC/DC normalization was used for compensating the difference in image intensities at the two wavelengths [see equations (2), (3)]. Referring now more particularly to FIG. 8C and FIG. 8D, FFT spectra of the simultaneously recorded PPGs at the two wavelengths show pronounced peaks at 1.5 Hz, which correspond to the heart rate.

Figure 9:
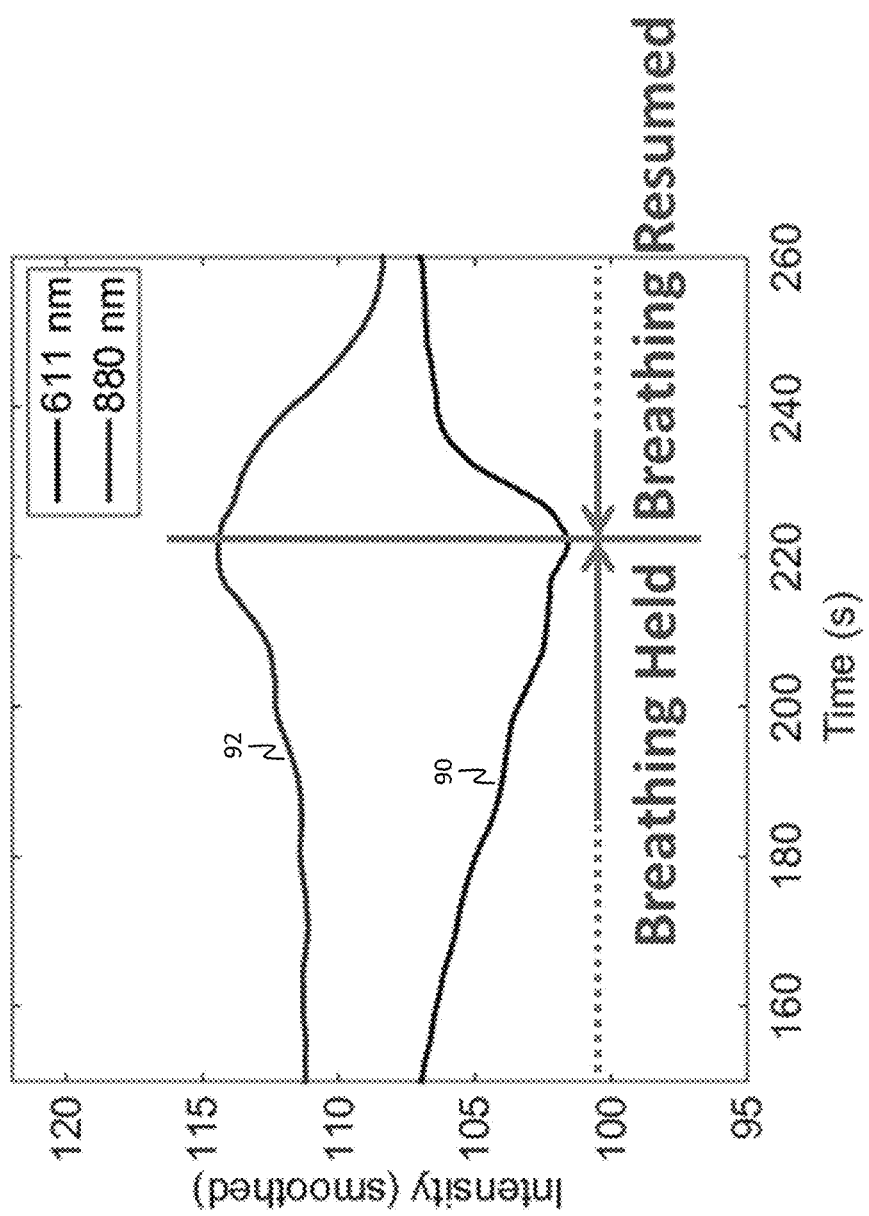
FIG. 9 shows an example of image intensity changes due to $SpO_2$ variation. Each PPG signal has been smoothed by a 100-point moving average filter.

Now referring to FIG. 9, an example of image intensity changes due to $SpO_2$ variation it is shown. Plotted are PPG signals 90, 92 at 611 nm and 880 nm, respectively. Each PPG signal has been smoothed by a 100-point moving average filter. When $SpO_2$ drops, $HbO_2$ concentration decreases, and Hb concentration increases. In this case, we expect that more orange light and less NIR light will be absorbed. Consequently, the reflectance of orange light will drop and that of the NIR light will increase. When $SpO_2$ increases, opposite changes in the reflectance are expected. Plot 92 shows that the average intensity at 880 nm increased when the subject held breath ($SpO_2$ dropped) and decreased after the subject resumed breathing ($SpO_2$ increased). Plot 90 shows an opposite trend at 611 nm. These observations are consistent with the optical absorption properties of $HbO_2$ and Hb at 611 and 880 nm.

$SpO_2$ Measurement

Figure 10B:
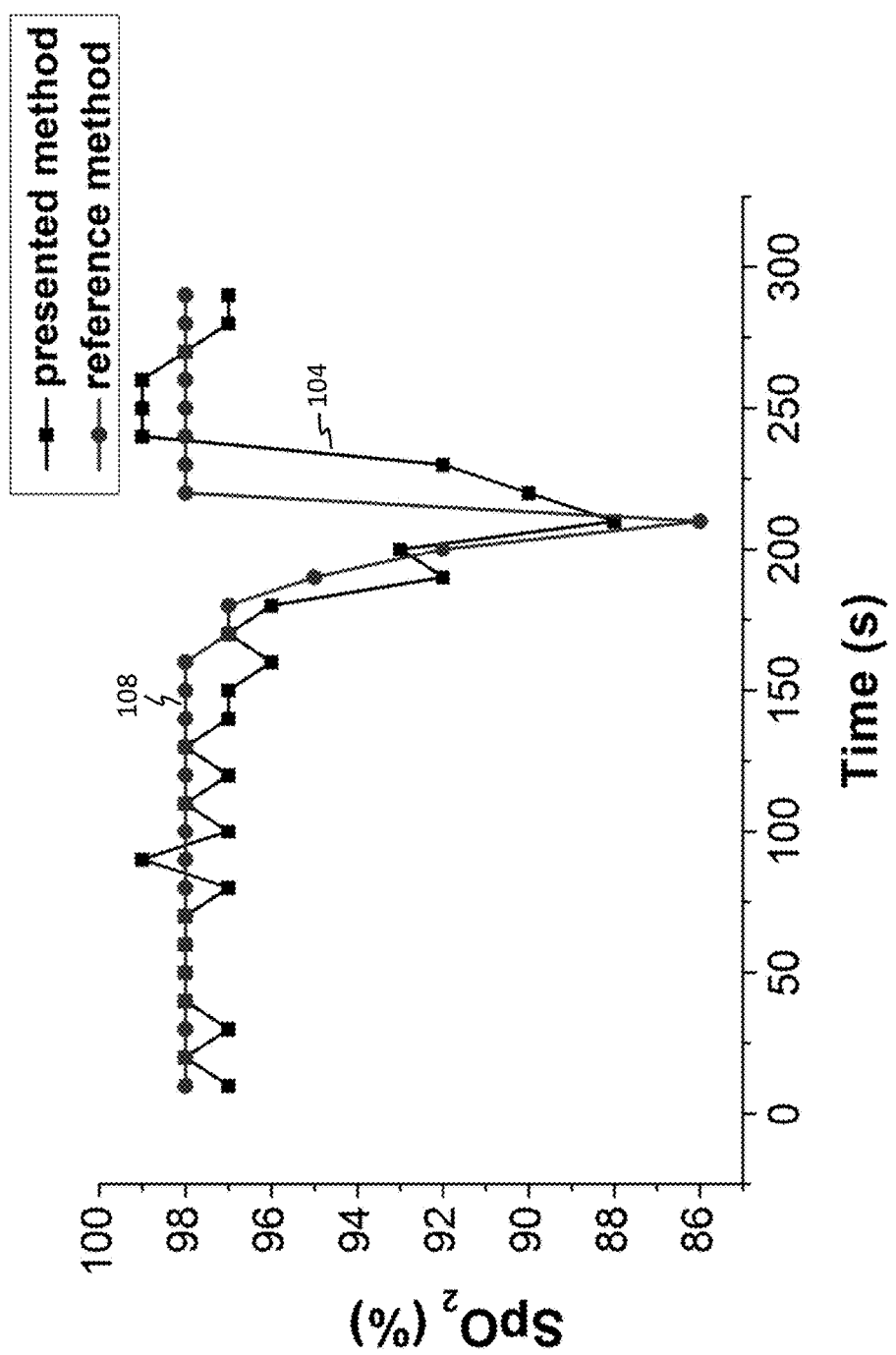

Now referring jointly to FIG. 10A and FIG. 10B, examples of $SpO_2$ measured using a pulse oximeter (reference method) and using the new method disclosed herein are shown. Two sets of measurements performed for validation purpose, wherein $SpO_2$ values were obtained and plotted against time using the presented method as plotted on curves 106, 108 and were compared against those obtained using the reference device as plotted on curves 102, 104 every 10 s over a 5-min measurement duration. The comparisons shown indicate that the $SpO_2$ measured using the noncontact method is consistent with that measured using the contact-based reference method. The stable $SpO_2$ value at 98% corresponds to the normal breathing period of 2 min and the evident reduction corresponds to the time period for which breath is held. The $SpO_2$ value restoration corresponds to the resumption of normal breathing. A delay (~10 s) in the reading of the reference pulse oximeter was corrected for comparison with the noncontact $SpO_2$ detection.

Small-Scale Pilot Study

Figure 11:
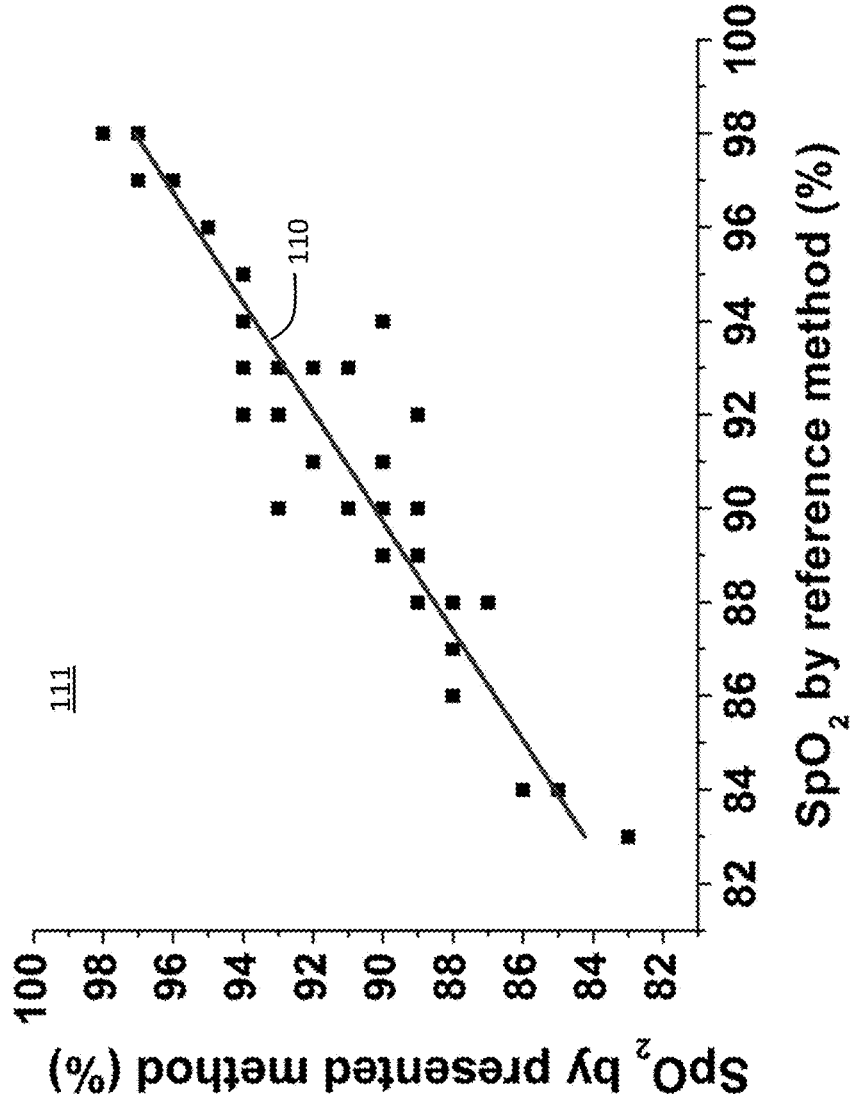
FIG. 11 shows an example of correlation between the lowest $SpO_2$ values obtained from the presented noncontact and reference contact methods.

Referring now to FIG. 11, an example of correlation between the lowest $SpO_2$ values obtained from the presented noncontact and reference contact methods. Line 110 is a linear fit of the data points. To demonstrate the robustness of the disclosed noncontact method to monitor $SpO_2$, a small-scale pilot study was conducted and statistical analysis of the data was completed. Six subjects were enrolled in the Institutional Review Board study approved by Arizona State University (No. STUDY00002240). The subjects included different genders (three males, three females), ages (27.3±2.8 years old, mean±SD), and skin colors. Informed consents were obtained from all the subjects following an approved protocol. None of the subjects had any known respiratory disease. The test was repeated as described above on different subjects and the lowest $SpO_2$ values were compared as determined by using the presented method and reference pulse oximetry. Plot 111 is a plot of the lowest $SpO_2$ values from 43 tests and linear least square regression. A good linear correlation ($R^2$=0.87) was found between the presented and reference methods over a wide range of oxygen saturation levels. Slope of the linear fitting curve is about 0.86, which is small than the ideal value of 1, with standard error of 0.05. The data are dispersed around the fitted linear curve 110, which may be attributed to subject movement, and light scattering effects.

Figure 12:
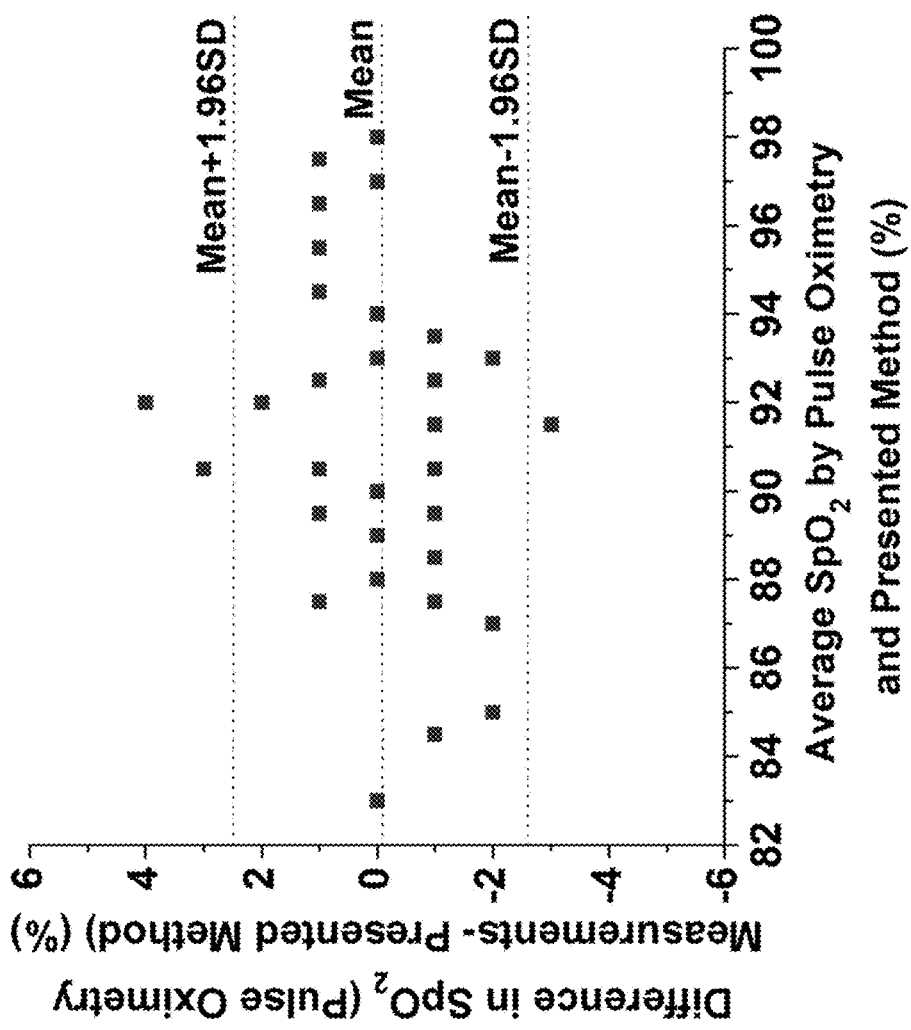
FIG. 12 shows an example of a Bland-Altman plot showing the difference between the $SpO_2$ values measured using the presented noncontact method and the commercial contact pulse oximetry versus the average values of the two methods.

Now referring to FIG. 12, an example of a Bland-Altman plot showing the difference between the $SpO_2$ values measured using the presented noncontact method and the commercial contact pulse oximetry versus the average values of the two methods is presented. The mean of the differences between the presented method and reference method is −0.07%. The interval for 95% limits of agreement between the two methods is from −2.65% to 2.51%, which is calculated by mean difference ±1.96 x standard deviation of the differences. The root-mean square error is 1.3 and r is 0.936 ($p<0.001$). Since $p<0.05$ indicates a significant correlation between the two methods under comparison, we conclude that the observed correlation between our noncontact $SpO_2$ detection method and the traditional contact pulse oximetry is statistically significant. The lowest $SpO_2$ observed during testing for this study was 83%. Lower $SpO_2$ values were difficult to achieve by holding breath in healthy individuals. A person with $SpO_2$ lower than 80% is considered to be in a state of hypoxia. Our method was validated for $SpO_2$ values ranging from 83%-100%, which is the normal oxygen saturation level range in most healthy individuals. Thus, the presented method can be used for daily $SpO_2$ monitoring.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

REFERENCES

The teachings of the following publications are incorporated herein in their entirety by this reference.

[1] M. Tavakoli et al., "An ultra-low-power pulse oximeter implemented with an energy-efficient transimpedance amplifier," IEEE Trans. Biomed. Circuits Syst., vol. 4, no. 1, pp. 27-38, January 2010.

[2] Understanding Continuous Mixed Venous Oxygen Saturation (SvO2) Monitoring With the Swan-Ganz Oximetry TD System, Edwards Life-sciences LLC, Irvine, Calif., USA, 2002, p. 1.

[3] What Does $SpO_2$ Mean? What is the Normal Blood Oxygen Level?" Withings, Issy-les-Moulineaux, France (2015). [Online]. Available: withins.zendesk.com.

[4] D. Shao et al., "Noncontact monitoring breathing pattern, exhalation flow rate and pulse transit time," IEEE Trans. Biomed. Eng., vol. 61, no. 11, pp. 2760-2767, November 2014.

[5] M.-Z. Poh et al., "Advancements in noncontact, multi-parameter physiological measurements using a webcam," IEEE Trans. Biomed. Eng., vol. 58, no. 1, pp. 7-11, January 2011.

[6] W. Verkruysse et al., "Remote plethysmographic imaging using ambient light," Opt. Exp., vol. 16, no. 26, pp. 21434-21445, December 2008.
[7] V. Kamat, "Pulse oximetry," Indian J. Anaesth., vol. 46, no. 4, pp. 261-268, 2002.
[8] P. E. Bickler et al., "Effects of skin pigmentation on pulse oximeter accuracy at low saturation," Anesthesiology, vol. 102, no. 4, pp. 715-719, 2005.
[9] K. Humphreys et al., "A CMOS camera-based pulse oximetry imaging system," in Proc. IEEE Eng. Med. Biol. Soc. Conf., Shanghai, China, 2005, vol. 4, pp. 3494-3497.
[10] K. Humphreys et al., "Noncontact simultaneous dual wavelength photoplethysmography: A further step toward noncontact pulse oximetry," Rev. Sci. Instrum., vol. 78, no. 4, p. 044304, 2007.
[11] F. P. Wieringa et al., "Contactless multiple wavelength photoplethysmographic imaging: A first step toward 'SpO$_2$ camera' technology," Ann. Biomed. Eng., vol. 33, no. 8, pp. 1034-1041, 2005.
[12] L. Kong et al., "Non-contact detection of oxygen saturation based on visible light imaging device using ambient light," Opt. Exp., vol. 21, no. 15, pp. 17464-17471, 2013.
[13] L. Tarassenko et al., "Non-contact video-based vital sign monitoring using ambient light and auto-regressive models," Physiol. Meas., vol. 35, no. 5, pp. 807-831, 2014.
[14] U. Bal, "Non-contact estimation of heart rate and oxygen saturation using ambient light," Biomed. Opt. Exp., vol. 6, no. 1, pp. 86-97, December 2014.
[15] U. S. Freitas, "Remote camera-based pulse oximetry," in Proc. 6th Int. Conf. eHealth, Telemed., Social Med., Barcelona, Spain, 2014, pp. 59-63.
[16] J. Lee et al., "Comparison between red, green and blue light reflection photoplethysmography for heart rate monitoring during motion," in Proc. IEEE Eng. Med. Biol. Soc. Conf., 2013, pp. 1724-1727.
[17] J. Jiang et al., "What is the space of spectral sensitivity functions for digital color cameras?" in Proc. Workshop Appl. Comput. Vis., 2013, pp. 168-179.
[18] H.-Yi Tsai et al., "A study on oxygen saturation images constructed from the skin tissue of human hand," in Proc. IEEE Int. Instrum. Meas. Technol. Conf., Minneapolis, Minn., USA, May 2013, pp. 58-62.
[19] H.-Y. Tsai et al., "A noncontact skin oxygen-saturation imaging system for measuring human tissue oxygen saturation," IEEE Trans. Instrum. Meas., vol. 63, no. 11, pp. 2620-2631, November 2014.
[20] S. Prahl, Optical Absorption of Hemoglobin, Oregon Medical Laser Center, Portland, Oreg., USA (1998). [Online]. Available: http://omlc.org/spectra/hemoglobin/summary.html
[21] G. M. Azmal et al., "Continuous measurement of oxygen saturation level using photoplethysmography signal," in Proc. IEEE Int. Conf. Biomed. Pharmaceutical Eng., Singapore, 2006, pp. 504-507.
[22] C. G. Scully et al., "Physiological parameter monitoring from optical recordings with a mobile phone," IEEE Trans. Biomed. Eng., vol. 59, no. 2, pp. 303-306, February 2012.
[23] L. F. C. Martinez et al., "Optimal wavelength selection for noncontact reflection photoplethysmography," in Proc. SPIE, 22nd Congr. Int. Commission Opt., vol. 8011, p. 801191 November 2011.
[24] W. S. Johnston, "Development of a signal processing library for extraction of SpO2, HR, HRV, and RR from photoplethysmographic waveforms," M.S. thesis, Dept. Biomed. Eng., Worcester Polytechnic Inst., Worcester, Minn., USA, 2006.
[25] T. L. Rusch et al., "Alternate pulse oximetry algorithms for SpO$_2$ computation," in Proc. IEEE Eng. Med. Biol. Soc. Conf., Baltimore, Md., USA, November 1994, vol. 2, pp. 848-849.
[26] J. E. Scharf et al., "Pulse oximetry through spectral analysis," in Proc. 12th Southern Biomed. Eng. Conf., New Orleans, La., USA, April 1993, pp. 227-229.
[27] J. E. Scharf and T. L. Rusch, "Optimization of portable pulse oximetry through Fourier analysis," in Proc. 12th Southern Biomed. Eng. Conf., New Orleans, La., USA, April 1993, pp. 233-235.
[28] T. L. Rusch et al., "Signal processing methods for pulse oximetry," Comput. Biol. Med., vol. 26, no. 2, pp. 143-159, 1996.
[29] J. M. Kim et al., "Signal processing using Fourier & wavelet transform for pulse oximetry," in Proc. Conf. Lasers Electro-Opt., Chiba, Japan, 2001, vol. 2, pp. 310-311.
[30] Y. Sun et al., "Motion-compensated noncontact imaging photoplethysmography to monitor cardiorespiratory status during exercise," J. Biomed. Opt., vol. 16, no. 7, p. 077010, 2011.
[31] L. Feng et al., "Motion-resistant remote imaging photoplethysmography based on the optical properties of skin," IEEE Trans. Circuits Syst. Video Technol., vol. 25, no. 5, pp. 879-891, May 2015.
[32] J. G. Webster, Design of Pulse Oximeters. London, U.K.: Institute of Physics Publishing, 1997.
[33] I. Fine and A. Weinreb, "Multiple scattering effect in transmission pulse oximetry," Med. Biol. Eng. Comput., vol. 33, no. 5, pp. 709-712, 1995.
[34] G. Zonios et al., "Pulse oximetry theory and calibration for low saturations," IEEE Trans. Biomed. Eng., vol. 51, no. 5, pp. 818-822, May 2004.

What is claimed is:

1. A device for non-contact measurement of blood oxygen saturation (SpO$_2$) in a human subject having a face, comprising:
a camera;
a microcontroller;
an illumination system, coupled to receive control signals from the microcontroller, consisting of a first LED array placed proximate the left side of the camera and a second LED array symmetrically placed proximate the right side of the camera each of the first and second LED arrays having a first plurality of rows of NIR LEDs emitting near infrared (NIR) light, and a second plurality of rows of orange LEDs emitting orange light alternating with the first plurality of rows of NIR LEDs, where the first and second LED arrays are located in optical paths adapted to transmit reflected light from the face to the camera;
wherein the microcontroller is connected to the first and second LED arrays to generate control signals for alternately switching the NIR LEDs and orange LEDs on and off for both the first and second LED arrays;
wherein the microcontroller is also coupled to transmit a camera trigger to the camera, where the camera generates video signal values sensed from the reflected light where the reflected light includes pulsatile components and non-pulsatile components;
a processor for receiving the video signal values from the camera; and wherein the processor determines $SpO_2$ values that are proportional to the ratios of the absorbance of the NIR LEDs and the orange LEDs as transmitted in the reflected light.

2. The device of claim 1, wherein the NIR LEDS comprise a plurality of LEDs having an emitted nominal wavelength of 880 nm, and the orange LEDs have an emitted wavelength in the range of 590 nm to 635 nm.

3. The device of claim 1, wherein the camera captures an image at the camera's trigger signal rising edge when either the NIR or the orange LEDs are illuminated.

4. The device of claim 3, wherein the camera comprises a monochromatic camera.

5. The device of claim 3, wherein the camera captures an image at 10 frames/s.

6. A method for non-contact measurement of blood oxygen saturation ($SpO_2$) in a human subject having a face, comprising:
locating an illumination system consisting of a first LED array and a second LED array placed respectively on the left and right sides of a camera each of the first and second LED arrays having alternating rows of NIR LEDs emitting near infrared (NIR), and orange LEDs emitting orange light in an optical path adapted to transmit reflected light from the face to the camera;
transmitting reflected light from the face to the camera by alternately illuminating the NIR LEDs and orange LEDs for both the first and second LED arrays;
operating the camera to capture the reflected light to produce a plurality of video signal values;
processing the video signal values from the camera, wherein the video signal values include pulsatile components and non-pulsatile components; and
determining $SpO_2$ values from the video signal values as proportional to the ratios of the absorbance of the NIR light and the orange light after they are emitted from the first and second LED arrays and then reflected from the face.

7. The method of claim 6, wherein illuminating the first and second arrays of LEDs comprises illuminating the rows of NIR LEDS including a plurality of LEDs having a nominal emitted wavelength centered around 880 nm, and the rows of orange LEDs including an emitted wavelength in the range of 590 nm to 635 nm.

8. The method of claim 6, wherein operating the camera comprises transmitting camera trigger signals to the camera.

9. The method of claim 8, wherein operating the camera further comprises capturing an image when the camera's trigger signal produces a rising edge when either the NIR or the orange LEDs are illuminated.

10. The method of claim 9, wherein the act of capturing an image comprises capturing a monochromatic image.

11. The method of claim 9 wherein the act of capturing an image comprises capturing reflected light from a region of interest including upper and lower lips of the face.

12. The method of claim 11 wherein the region of interest comprises an area of 160 pixels×120 pixels around the upper and lower lips.

* * * * *